(12) United States Patent
Jozefiak

(10) Patent No.: US 11,975,019 B2
(45) Date of Patent: *May 7, 2024

(54) SULFATED GLYCOSAMINOGLYCAN BIOMATERIALS AS PROTEOGLYCAN MIMICS

(71) Applicant: Glycologix, LLC, Beverly, MA (US)

(72) Inventor: Thomas H. Jozefiak, Belmont, MA (US)

(73) Assignee: Glycologix, Inc., Beverly, MA (US)

( * ) Notice: Subject to any disclaimer, the term of this patent is extended or adjusted under 35 U.S.C. 154(b) by 146 days.

This patent is subject to a terminal disclaimer.

(21) Appl. No.: 17/372,102

(22) Filed: Jul. 9, 2021

(65) Prior Publication Data

US 2022/0000905 A1 Jan. 6, 2022

Related U.S. Application Data

(60) Division of application No. 16/295,073, filed on Mar. 7, 2019, now Pat. No. 11,090,327, which is a continuation of application No. PCT/US2017/051799, filed on Sep. 15, 2017.

(60) Provisional application No. 62/395,805, filed on Sep. 16, 2016.

(51) Int. Cl.
| | | |
|---|---|---|
| A61K 31/726 | (2006.01) | |
| A61K 9/00 | (2006.01) | |
| A61K 47/61 | (2017.01) | |
| A61P 13/10 | (2006.01) | |
| C07C 317/08 | (2006.01) | |
| C08B 15/00 | (2006.01) | |
| C08B 37/00 | (2006.01) | |
| C08B 37/08 | (2006.01) | |

(52) U.S. Cl.
CPC .......... *A61K 31/726* (2013.01); *A61K 9/0019* (2013.01); *A61K 47/61* (2017.08); *A61P 13/10* (2018.01); *C07C 317/08* (2013.01); *C08B 15/005* (2013.01); *C08B 37/0063* (2013.01); *C08B 37/0072* (2013.01)

(58) Field of Classification Search
CPC .... C08B 37/0063–0075; A61K 31/726; A61K 31/727; A61K 31/736; A61K 31/737; A61K 47/36; A61K 47/38; A61K 47/61; A61K 9/0019; A61P 13/10; A61P 17/02; A61P 19/02; A61P 27/20; A61L 27/3658; A61L 27/3679; A61L 27/54
See application file for complete search history.

(56) References Cited

U.S. PATENT DOCUMENTS

| | | | |
|---|---|---|---|
| 4,863,907 A | 9/1989 | Sakurai et al. | |
| 5,510,418 A | 4/1996 | Rhee et al. | |
| 5,955,578 A * | 9/1999 | Pierschbacher | A61P 43/00 530/355 |
| 6,281,341 B1 | 8/2001 | Mares-Guia et al. | |
| 8,912,149 B1 | 12/2014 | Rawat et al. | |
| 9,200,039 B2 | 12/2015 | Vazquez-Portalatin et al. | |
| 2003/0212042 A1 | 11/2003 | Lassila et al. | |
| 2006/0234978 A1* | 10/2006 | Marcum | A61K 31/737 514/54 |
| 2015/0306237 A1* | 10/2015 | Gurny | A61K 31/728 536/55.1 |
| 2016/0051692 A1* | 2/2016 | Marcolongo | A61K 38/1732 424/78.27 |

FOREIGN PATENT DOCUMENTS

| | | |
|---|---|---|
| EP | 0830416 A1 | 3/1998 |
| EP | 1607405 A1 | 12/2005 |
| EP | 3040117 A1 | 7/2016 |
| EP | 3187510 A1 | 7/2017 |
| JP | S61138601 A | 6/1986 |
| JP | S61164558 A | 7/1986 |
| JP | 2006517928 A | 8/2006 |
| JP | 2009011814 A | 1/2009 |
| JP | 2009538287 A | 11/2009 |
| WO | 2008070640 A1 | 6/2008 |
| WO | 2015115609 A1 | 8/2015 |
| WO | 2015142721 A1 | 9/2015 |

OTHER PUBLICATIONS

Wang, H. et al "Acceleration of wound healing in acute full-thickness skin wounds . . . " Burns & Trauma, vol. 2, iss 4, pp. 181-186. (Year: 2014).*

Verduzco, R. et al "Structure, function, self-assembly and applications of bottlebrush copolymers" Chem. Soc. Rev., vol. 44, pp. 2405-2420. (Year: 2015).*

Chang, K. Y. et al., "Fabrication and characterization of poly (y-glutamic acid)-graft-chondroitin sulfate/polycaprolactone porous scaffolds for cartilage tissue engineering", Acta Biomaterialia, vol. 5, No. 6, Jul. 1, 2009, 1937-1947.

Cheng, F. et al., "A versatile method for functionalizing surfaces with bioactive glycans", Bioconjug. Chem., 22(1), Jan. 19, 2011, 50-57.

Kiang, W. et al., "Fractionation and Properties of a Chondroitin Sulfate Proteoglycan and the Soluble Glycoproteins of Brain", J. Biol. Chem., vol. 256, No. 20, 1981, 10529-10537.

(Continued)

*Primary Examiner* — Leigh C Maier

(74) *Attorney, Agent, or Firm* — Elmore Patent Law Group; Carolyn S. Elmore; Jia Kang

(57) ABSTRACT

Polymer conjugates are provided that are capable of mimicking functions of natural proteoglycans found in the extracellular matrix of connective tissues. The polymer conjugates of the invention have utility in treating a subject suffering soft tissue conditions. Also provided are simple and scalable chemical processes for the preparation of the polymer conjugates of the invention.

13 Claims, 6 Drawing Sheets

Specification includes a Sequence Listing.

(56) References Cited

OTHER PUBLICATIONS

Li, Q. et al., "Photocrosslinkable Polysaccharides Based on Chondroitin Sulfate", Journal of Biomedical Materials Research, vol. 68, No. 1, 2004, 28-33.
Lindstedt, K. et al., "Soluble heparin proteoglycans released from stimulated mast cells induce uptake of low density lipoproteins by macrophages via scavenger receptor-mediated phagocytosis", J. Lipid Res., vol. 33, 1992, 65-75.
Liu, L-S. et al., "Local Sustained Release of Growth Factors From an Implantable Chondroitin Sulfate Scaffold for Tissue Regen Era Ton", Proceedings of the International Symposium on Controlled Release Bioactive Materials, Controlled Release Society, Inc, US; KR, vol. 24, 1997, 577-578.
Place, L. et al., "Synthesis and Characterization of Proteoglycan-Mimetic Graft Copolymers with Tunable Glycosaminoglycan Density", Biomacromolecules, vol. 15, 2014, 3772-3780.
Sintov, A. et al., "Cross-linked chondroitin sulphate: characterization for drug delivery purposes", Biomaterials, vol. 16, No. 6, 1995, 473-478.
Tsai, M-F. et al., "Characterization of hydrogels prepared from copolymerization of the different degrees of methacrylate-grafted chondroitin sulfate macromers and acrylic acid", Journal of Biomedical Materials Research Part A, vol. 84A, No. 3, Mar. 1, 2008, 727-739.
Wang, S-C. et al., "Characterization of chondroitin sulfate and its interpenetrating polymer network hydrogels for sustained-drug release", International Journal of Pharmaceutics, vol. 329, No. 1-2, Dec. 20, 2006, 103-109.

\* cited by examiner

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Arg Gly Asp Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
Pro His Ser Arg Asn
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Glu Asp Val
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Ile Gly Ser Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ile Ile Phe Phe Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Lys Val Ala Val
1               5

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Tyr Ile Arg Ile Ala Asp Thr Asn Ile Thr Gly Cys
1               5                   10

<210> SEQ ID NO 8
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 8

Leu Arg Glu Leu His Leu Asn Asn Asn
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu His Glu Arg His Leu Asn Asn Asn
1               5

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Leu Arg Ser Lys Ser Lys Lys Phe Arg Arg Pro Asp Ile Gln Tyr
1               5                   10                  15

Pro Asp Ala

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg Ala Asn Ala Ala Leu Lys Ala Gly Glu Leu Tyr Lys Ser Ile
1               5                   10                  15

Leu Tyr Gly Cys
            20

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Tyr Arg Gly Arg Leu Gly Cys
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

Lys Glu Leu Asn Leu Val Tyr Thr Gly Cys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ser Ile Thr Thr Ile Asp Val Pro Trp Asn Val Gly Cys
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp His Cys Tyr Thr Tyr Phe Pro His His Tyr Cys Val Tyr Gly
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Trp His Cys Tyr Thr Tyr Phe Pro His His Tyr Cys Thr Tyr Gly
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Trp His Cys Tyr Thr Tyr Phe Pro His His Tyr Cys Val Tyr Gly
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Trp His Cys Tyr Thr Tyr Phe Pro His His Tyr Cys Val Tyr Gly
1               5                   10                  15

<210> SEQ ID NO 19
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 19

Tyr Trp His Cys Tyr Thr Tyr Phe Pro His His Tyr Cys Val Tyr Gly
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ala His Trp Gln Phe Asn Ala Leu Thr Val Arg Gly Gly Gly Cys
1               5                   10                  15
```

SULFATED GLYCOSAMINOGLYCAN BIOMATERIALS AS PROTEOGLYCAN MIMICS

RELATED APPLICATIONS

This application is a divisional of U.S. application Ser. No. 16/295,073, filed Mar. 7, 2019, which is a continuation of International Application No. PCT/US2017/051799, which designated the United States and was filed on Sep. 15, 2017, published in English, which claims the benefit of U.S. Provisional Application No. 62/395,805 filed on Sep. 16, 2016. The entire teachings of the above applications are incorporated herein by reference.

BACKGROUND

The extracellular matrix (ECM) forms the non-cellular scaffolding of soft and connective tissues. It provides both the biochemical and structural support needed by resident cells and it plays a critical role in maintaining tissue shape and resisting mechanical stress. Proteoglycans are native macromolecules of the ECM that maintain tissue health and prevent ECM degradation. Through their strong osmotic hydration and ability to bind and modulate key growth factors, proteoglycans are the protectors of a healthy ECM. As a response to aging, disease, or damage, the ECM loses functionality. Proteoglycan content diminishes and with it collagen fibers and other matrix components also begin to degrade. Such degradation is an underlying factor in a number of soft tissue diseases, disorders, and/or conditions, including those of the skin, spinal disc, cartilage, and urethral tissue to name but a few. The restoration of proteoglycan functionality is one option for addressing the loss of ECM functionality.

SUMMARY OF THE INVENTION

The present disclosure describes polymer conjugates of moderate to high molecular weight that are soluble in aqueous and biological solutions and are comprised of sulfated glycosaminoglycan (GAG) chains. Provided polymer conjugates are biocompatible, easy to inject using small gauge needles, and are capable of mimicking certain proteoglycan functions in soft tissue ECM. In some cases, provided polymer conjugates comprise sulfated GAG chains as well as biocompatible natural and synthetic polymers. In some embodiments, GAG chains are chemically modified with therapeutically useful groups. The present disclosure also provides methods of making said polymer conjugates, including, among others, a simple 1-pot aqueous chemical process that can be scaled to produce commercially relevant quantities of material. The present disclosure also provides methods of treating subjects suffering from soft tissue degenerative conditions.

DETAILED DESCRIPTION OF CERTAIN EMBODIMENTS

Figure 1:
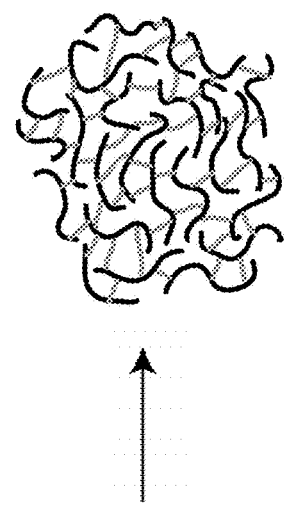
FIG. 1 is a schematic showing the formation of an extended crosslinked network.
Figure 1:
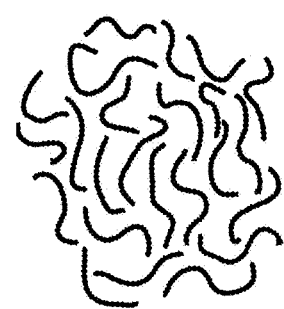

In order to address a long-felt need in the treatment of soft tissues diseases, disorders, and conditions, it is desirable to produce proteoglycan mimics that are capable of mimicking the morphology and physical properties of natural proteoglycans. Natural proteoglycans are comprised of GAG chains that are highly negatively charged under physiological conditions due to the presence of sulfate and carboxylate groups.

Prior to the instant disclosure, polymer conjugates comprised of sulfated GAG chains linked by multifunctional linking agents to form a predominantly soluble product (i.e., not an extended crosslinked network) were not exemplified. The present invention encompasses the recognition that under certain conditions, sulfated GAGs can react with linking agents in a controlled way to produce high molecular weight, branched, sulfated GAG compositions that remain soluble in aqueous solution. The molecular weight of such polymer conjugates can be characterized using standard methodologies for soluble polymers: gel permeation chromatography and dynamic light scattering. Such soluble, branched, high molecular weight sulfated GAGs are not currently available and have not previously been described. They have utility as proteoglycan mimics in treating numerous indications as described above.

Definitions

As used herein, headers and section subtitles are provided for organizational purposes and are not meant to be limiting. Therefore, embodiments described in one section apply to the entirety of the application, unless otherwise specified.

The term "approximately" or "about", as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "administration", as used herein, typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravesical, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

As used herein, "biocompatible" is intended to describe materials that exert minimal destructive or host response effects while in contact with body fluids or living cells or tissues. The term is also taken to mean that which results in minimal interactions with recognition proteins, e.g., naturally occurring antibodies, cell proteins, cells and other components of biological systems, unless such interactions are specifically desirable. Thus, materials and functional groups specifically intended to cause the above effects and whose administration in vivo induces minimal and medically acceptable inflammation, foreign body reaction, immunotoxicity, chemical toxicity or other such adverse effects are considered to be biocompatible.

The term "biomolecule", as used herein, refers to molecules (e.g., proteins, amino acids, peptides, polynucleotides, nucleotides, carbohydrates, sugars, lipids, nucleoproteins, glycoproteins, lipoproteins, steroids, etc.) which belong to classes of chemical compounds, whether naturally-occurring or artificially created (e.g., by synthetic or recombinant methods), that are commonly found in cells and tissues. Exemplary types of biomolecules include, but are not limited to, peptides, enzymes, receptors, neurotransmitters, hormones, cytokines, cell response modifiers such as growth factors and chemotactic factors, antibodies, vaccines, interferons, ribozymes, anti-sense agents, plasmids, DNA, and RNA.

The term "treatment" (also "treat" or "treating"), as used herein, refers to any administration of a substance (e.g., pharmaceutical composition) that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder, and/or condition and/or of a subject who exhibits only early signs of the disease, disorder, and/or condition. Alternatively or additionally, such treatment may be of a subject who exhibits one or more established signs of the relevant disease, disorder, and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

As used herein "subject" means an organism, typically a mammal (e.g., a human). In some embodiments, a subject is suffering from a relevant disease, disorder, or condition. In some embodiments, a subject is susceptible to a disease, disorder, or condition. In some embodiments, a subject displays one or more symptoms or characteristics of a disease, disorder, or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered. In some embodiments, for any of the methods described herein, a subject is a mammal. In some embodiments, for any of the methods described herein, a subject is a human.

The terms "glycosaminoglycan" and "GAG", as used interchangeably herein, refer to a polysaccharide comprised of a repeating disaccharide unit comprising an amino sugar (such as N-acetylglucosamine or N-acetylgalactosamine), and a uronic sugar (such as glucuronic acid or iduronic acid), or galactose. The GAGs for use in the present invention may vary in size and be either sulfated or non-sulfated. The GAGs which may be used in the methods of the invention include, but are not limited to, hyaluronic acid, chondroitin, chondroitin sulfates (e.g., chondroitin 6-sulfate and chondroitin 4-sulfate), heparan, heparan sulfate, heparin, dermatan, dermatan sulfate, keratan sulfate, and the like.

The terms "improve," "increase" or "reduce", as used herein or grammatical equivalents thereof, indicate values that are relative to a baseline measurement, such as a measurement in the same individual prior to initiation of a treatment described herein, or a measurement in a control individual (or multiple control individuals) in the absence of the treatment described herein.

As used herein, the term "modifier" refers to an organic, inorganic or bioorganic moiety that is covalently attached to a polymer conjugate. Modifiers can be small molecules or macromolecules, and can belong to any chemical or pharmaceutical class, e.g., nucleotides, chemotherapeutic agents, antibacterial agents, antiviral agents, immunomodulators, hormones or analogs thereof, enzymes, inhibitors, alkaloids and therapeutic radionuclides a therapeutic radionuclide (e.g., alpha, beta or positron emitter). In certain embodiments, modifiers according to the invention include, but are not limited to, biomolecules, small molecules, therapeutic agents, pharmaceutically useful groups or entities, macromolecules, diagnostic labels, chelating agents, hydrophilic moieties, dispersants, charge modifying agents, viscosity modifying agents, surfactants, coagulation agents and flocculants, to name a few. In some embodiments, a modifier is a target peptide having affinity for a particular biomolecule or tissue, and may enhance delivery and/or efficacy of a polymer conjugate. A modifier can have one or more pharmaceutical functions, e.g., biological activity and pharmacokinetics modification.

Pharmacokinetics modifiers can include, for example, antibodies, antigens, receptor ligands, hydrophilic, hydrophobic or charged groups. Biologically active modifiers include, for example, therapeutic drugs and prodrugs, antigens, immunomodulators. Detectable modifiers include diagnostic labels, such as radioactive, fluorescent, paramagnetic, superparamagnetic, ferromagnetic, X-ray modulating, X-ray-opaque, ultrasound-reflective, and other substances detectable by one of available clinical or laboratory methods, e.g., scintigraphy, NMR spectroscopy, MRI, X-ray tomography, sonotomography, photoimaging, radioimmunoassay.

The term "prevent" or "prevention", as used herein when used in connection with the occurrence of a disease, disorder, and/or condition, refers to reducing the risk of developing the disease, disorder, and/or condition and/or to delaying onset of one or more characteristics or symptoms of the disease, disorder, or condition. Prevention may be considered complete when onset of a disease, disorder, or condition has been delayed for a predefined period of time.

The term "reference", as used herein, describes a standard or control relative to which a comparison is performed. For example, in some embodiments, an agent, animal, individual, population, sample, sequence, or value of interest is compared with a reference or control agent, animal, individual, population, sample, sequence, or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is aggrecan. In some embodiments, a reference is a polymeric starting material. In some embodiments, a reference is a null conjugation reaction. In some embodiments, the reference is a null conjugation reaction identical in all respects to formation of a provided polymer conjugate except for the omission of a linker agent.

The term "gel", refers to viscoelastic materials whose rheological properties distinguish them from solutions or solids. A composition is considered to be a gel if it does not flow under steady state or low shear conditions, but show some fluidity or flow when agitated. Gels consist of 3-dimensional extended networks that constitute a continuous solid phase into which a fluid phase is dispersed (water, in the case of a hydrogel). In general, the fluid phase is present in far greater quantity over the solid phase. The extended crosslinked network can be formed through either chemical covalent bonds, or physical associations in solution.

The term "molecular weight", unless otherwise specified, refers to weight average molecular weight or "Mw" (used interchangeably herein with "Mw").

The term "soluble", refers to the chemical condition of a molecule (solute) being completely dispersed at a molecular level in another substance (solvent) wherein there are no strong interactions between solute molecules.

Proteoglycans

Proteoglycans are glycoproteins found in the extracellular matrix (ECM) of all connective tissues of the body. A large number of proteoglycans and their tissue-specific expression have been identified. Although there is considerable diversity of structure, the common structural element of all proteoglycans is a protein core glycosylated with one or many sulfated glycosaminoglycan (GAG) chains. The protein core can contain several modular structural elements important for biological functions (e.g., IgG-like, EGF-like, HA-binding motif, leucine-rich motifs, etc.). The covalently bound sulfated GAG chains are most typically chondroitin sulfate, dermatan sulfate, keratan sulfate, or heparan sulfate. These are often attached to the protein core as O-linked glycans bound to a serine moiety on the core protein chain.

Hydration is critically important for ECM homeostasis. Water content determines tissue volume and resistance to compression. Hydration also creates space required for cellular migration, organization of ECM structural components such as collagen and elastin, and the transport of biomolecules. A major structural function of proteoglycans in the ECM is maintenance of hydration. This is particularly relevant for the large aggregating proteoglycans bearing a large number of sulfated GAG chains. Proteoglycans in the hyalectan family, such as aggrecan and versican contain multiple (e.g., about 10-100) GAG chains concentrated within specific sub units of the core protein. These unique biopolymer structures have a bottlebrush-like polymer architecture and a very high density of anionic charge derived from the large number of sulfate and carboxylate moieties on the GAG chains concentrated in a small volume. In addition to providing critical hydration and structural support in the ECM, proteoglycans are known to play a significant role in extracellular signaling. They are known to bind strongly with several growth factors, chemokines, and cytokines and influence signaling pathways for apoptosis, cellular development, cell motility and adhesion.

A growing body of scientific evidence supports a significant role for proteoglycans in maintaining connective tissue integrity: protecting against tissue degradation, promoting healing after injury, and resisting disease. Because of the important role proteoglycans play in determining the physical properties of connective tissues, and the understanding that age-related changes in connective tissues such as the dermis correlate with proteoglycan degradation, proteoglycan-based therapeutics such as proteoglycan-replacement therapy are a promising approach for treating age-related changes and wound healing, and in addressing unmet medical needs in dermatology, urology, cardiovascular, and orthopedic areas.

Although proteoglycans are understood to be critically important biomolecules in the ECM of cartilage and soft tissues, they are present only in small quantity in most tissues. Proteoglycans are difficult to isolate from natural sources and purify at large scale. Hence, biomolecules such as aggrecan are currently available only as research tools in small quantity. Use of tissue-isolated proteoglycans as therapeutics is cost prohibitive and impractical. Moreover, proteoglycans extracted from xenobiotic tissues (bovine, porcine, marine) may be inappropriate for direct use in human medicine due to immunological host response.

Proteoglycan Mimic Materials

There have been several studies seeking to design compositions capable of mimicking the important structural and/or biological functions of naturally occurring proteoglycans (PG) in connective tissues. These approaches fall into a number of categories:

a. Sulfation of synthetic polymers or natural polysaccharides. For example, one of the simplest approaches for the synthesis of PG mimics is the sulfation of carbohydrates such as dextran [D Papy-Garcia, et. al., Macromolecules 2005, 38:4647-4654]. The sulfation of synthetic polymers such as aromatic polyphenols have also been reported to produce molecules with bioactivity of GAGs or PGs [UR Desai, Future Med. Chem. 2013, 5:1363-1366].

b. Attachment of sulfated GAGs to surfaces or particles. For example, chondroitin sulfate was conjugated to the surface of carbon nanotube to provide GAG-functional nanoparticles as PG mimics in a hydrogel construct for cartilage replacement [J Wei, et. al., Materials Chemistry and Physics 2015, 166:66-72]. Chondroitin sulfate was attached to surfaces of agarose gels after activation of those gels with a reactive cyanate ester capable of reacting with a serine moiety on the chondroitin sulfate reducing end [K J Mattern, et. al., Carbohydrate Research 2007, 342:2192-2201]. Chondroitin sulfate was attached to poly(ethylene terephthalate) fiber surfaces and chitosan-coated PET fiber surfaces [C-H Jou, et. al., Polym. Adv. Technol. 2005, 16:821-826].

c. Creation of insoluble particles by complexation of anionic sulfated GAGs with cationic polymers. The formation of a complex between highly anionic GAGs and polycations such as chitosan has been described as a method to generate nanoparticles capable of binding FGF-2 [S Boddohi, et. al., Biomacromolecules 2009, 10:1402-1409] [L W Place et al., Biomacromolecules 2014, 15:3772-3780]. Heparan was complexed with various reactive polymers to from an insoluble coating applied to medical device surfaces [US2005/0281857].

d. Conjugation of certain bioactive peptides with sulfated GAGs to provide well-defined, soluble peptidoglycan derivatives. For example, the conjugation of dermatan sulfate with peptides capable of binding either collagen-II or hyaluronic acid have been extensively explored and described [S Sharma, et. al., Acta Biomaterialia 2013, 9:4618-4625] [J C Bernhard, et. al., Acta Biomaterialia 2012, 8:1543-1550] [U.S. Pat. No. 9,200,039].

e. Polymerization of monomers bearing a sulfated disaccharide or oligosaccharide. For example, polymer mimics of chondroitin sulfate have been made via synthesis of ROMP polymerizable monomers substituted with a simple chondroitin sulfate disaccharide unit [S-G Lee, et, al., Chem. Sci., 2010, 1:322-325].

f. Synthesis of multivalent oligosaccharide glycans. Specific di- and tetra-saccharides representing single entity heparan sulfate (HS) structural motifs have been prepared and bound to a 4-arm dendritic linking molecule. These heparan sulfate mimics were found to have the ability to mimic the performance of long chain natural HS in their interactions with certain therapeutic proteins [PC Tyler, et. al., Angew. Chem. Int. Ed. 2015, 54: 2718-2723].

g. Conjugation of GAGs with other polymers. For example, several small sugars and oligo saccharides have been conjugated to synthetic polymers by the reaction of their reducing ends with complementary functionality on the synthetic polymer core [K Godula, et. al., J. Am. Chem. Soc. 2010, 132: 9963-9965]. In a related approach, aggrecan-like bottlebrush compositions have been reported using a hyaluronic acid derivative as a polymeric core capable of reacting with the reducing end of full length natural heparan or chondroitin sulfate chains as bristles [L W Place, et al., Biomacromolecules 2014, 15:3772-3780]. In another approach for forming a bottlebrush structure, chondroitin sulfate bearing an O-linked serine glycan at the reducing end of the chain has been used as a monotelechelic amine in several reaction scenarios including an amide forming reaction with poly(acrylic acid) as a core [US20130052155 A1].

A distinct area of research with some relevance to the field of proteoglycan mimics focuses on crosslinked GAG hydrogels. In these cases, extended crosslinked networks are obtained rather than soluble polymeric compounds. The properties of crosslinked networks are most fundamentally derived from their crosslink density and particle size. In contrast, soluble polymers are characterized by their molecular weight and degree of branching. In general, crosslinked gels have high modulus and can be difficult to administer by injection.

A water swollen hydrogel particle prepared through the crosslinking of a GAG material presents a GAG-rich surface in a biological environment. However, after injection into tissue these crosslinked gels behave as discrete particles within the ECM, and therefore cannot function as proteoglycan mimic materials. They do not have the ability to integrate into soft tissue and interact with other components of the ECM in the way a proteoglycan such as versican, for example, is known to do in the dermis.

A large majority of research on crosslinked GAG networks focuses on hyaluronic acid (HA), owing to its large scale production from bacterial culture as well as natural sources and commercial availability. Furthermore, HA is generally available in very high molecular weight form, usually above 500,000 Da and extending to several million Da. High molecular weight favors the formation of extended hydrogel structures. For this reason, there has been significant work on the synthesis and use of HA-based crosslinked hydrogels, and hyaluronic acid is by far the most widely used GAG in biopharma and medical device product development. HA gels are well known as dermal fillers, viscosupplements, and cosmetics.

In contrast to HA, sulfated GAGs (e.g., chondroitin sulfate, dermatan sulfate, heparan sulfate, and keratan sulfate), are currently only available from natural sources, and generally in much smaller quantity. Commercial sources of high quality GMP material are limited. Also, as extracted from natural tissues, these sulfated GAGs are found to have much lower molecular weight than HA. For example, bovine sourced chondroitin sulfate is generally found with molecular weight below 50,000 Da, and most typically below 25,000 Da. The low molecular weight of these biopolymers as well as the difficulty of sourcing high purity material has limited their use in biopharma and medical device product development.

Research reports and patents on crosslinked HA hydrogels have noted that other GAGs may be utilized in the place of HA. However, given the significant dissimilarities between sulfated GAGs and HA, most notably the very large difference in molecular weight, existing synthetic methods for forming gels with HA cannot be assumed to be applicable to sulfated GAGs. Also the properties of crosslinked hydrogels from sulfated GAGs cannot be assumed to resemble those of HA crosslinked hydrogels.

For the formation of crosslinked GAG hydrogels, several 1-step direct linking agents have been described in the literature and have been found to provide biocompatible hydrogels. These crosslinked HA hydrogels have been utilized in a variety of commercial products such as dermal fillers (e.g., HYLAFORM®, PREVELLE®, RESTYLANE®, JUVEDERM®) and viscosupplements (e.g., SYNVISC®, SYNVISC-ONE®, SUPARTZ®, EUFLEXXA®, JONEXA®, MONOVISC®, ORTHOVISC®) and adhesion barriers (e.g., INCERT®, INCERT-S®, HYALOBARRIER®). Non-limiting examples of direct linking agents are divinylsulfone (DVS), epichlorohydrin (epi), butanediol diglycidylether (BDDE), diepoxy octane, ethyleneglycol diglycidyl ether, phenylene-bis(ethyl carbodiimide), 1,1'carbonyldiimidazole (CDI).

The reaction of various direct crosslinkers with a sulfated GAG is known to form a strong hydrogel. However, Applicants have observed that such gel formation is sensitive to reaction conditions and unexpected results can be obtained. For example, the reaction of DVS with chondroitin sulfate may result in several outcomes. In some cases, a strong and clear gel is obtained. In some cases, a viscous clear fluid is obtained. In some cases, a cloudy suspension of an insoluble modified chondroitin sulfate is obtained. In some cases, a cloudy gel is obtained. Applicant discloses herein methods for controlling and directing these various outcomes to produce soluble polymer conjugates.

Despite the several attempts at developing proteoglycan mimic materials, there is currently no known polymer conjugate that effectively provides the beneficial physical and biological function of natural proteoglycans, is known or is expected to be biocompatible, is soluble and able to integrate into soft tissue by diffusion, is easy to inject or administer, is retained in soft tissue for an extended period of time, and can be made using an efficient and simple chemical process scalable to commercial quantities.

Polymer Conjugates

The present invention relates to the use of a number of different strategies to generate a proteoglycan mimic. The present invention encompasses the recognition that sulfated GAGs (and other polymers) contain a number of functional moieties that are capable of reaction with an appropriate linking agent to form soluble, higher order polymer conjugates, including those having branched and bottlebrush-like architectures. Such functional moieties may be reacted with a linking agent to "activate" a polymer chain for conjugation with one or more other polymer chains. While prior efforts on this front have generated GAG compositions that are gels, the present invention provides polymer conjugates that are not gels and remain soluble in aqueous solution. In some embodiments, soluble polymer conjugates of the present invention are produced by controlling the stoichiometry of the linking agent and sulfated GAG, the concentration of sulfated GAG, the molecular weight of the sulfated GAG, and/or and reaction time.

Functional moieties on a GAG or other polymers that may be utilized in linking chemistries described herein include, without limitation, hydroxyl groups, amines, thiols, and carboxyl groups. In some embodiments, a functional moiety is or comprises one or more hydroxyl groups along a GAG polymer backbone chain. In some embodiments, a functional moiety is or comprises one or more carboxyl groups along a GAG polymer backbone chain.

In some embodiments, polymer conjugates of the present invention comprise a plurality of sulfated GAG polymer chains linked via a linking agent. In some embodiments, polymer conjugates of the present invention comprise a plurality of sulfated GAG polymer chains and at least one additional polymer linked via a linking agent. In some embodiments, polymer conjugates of the present invention comprise a plurality of sulfated GAG polymer chains and at least two additional polymers linked via a linking agent. In some embodiments, polymer conjugates of the present invention comprise a plurality of sulfated GAG polymer chains and at least three additional polymers linked via a linking agent. In some embodiments, the sulfated GAG is chondroitin sulfate. In some embodiments, an additional polymer is a sulfated GAG other than chondroitin sulfate. In some embodiments, an additional polymer is a non-sulfated GAG. In some embodiments, an additional polymer is hyaluronic acid (HA) or carboxymethylcellulose (CMC).

It will be appreciated that polymer conjugates of the present invention will generally have higher (e.g., increased) molecular weight compared to an individual GAG polymer chain, but do not form a gel with an extended crosslinking network. In some embodiments, polymer conjugates of the present invention have a molecular weight in a particular range as compared with nonlinked sulfated GAG used as starting material (e.g., polymer conjugates having 3× to 100× the molecular weight of an individual, nonlinked sulfated GAG). In some embodiments, polymer conjugates of the present invention are branched multi-chained conjugates having a molecular weight in a particular range (e.g., 3× to 100× that of an individual, nonlinked sulfated GAG). In some embodiments, polymer conjugates of the present invention are bottlebrush-like multi-chained conjugates having a molecular weight in a particular range (e.g., 3× to 100× that of an individual, nonlinked sulfated GAG). In some embodiments, polymer conjugates of the present invention have a molecular weight in a range between about 3× to 100×, 3× to 75×, 3× to 50×, 3× to 25×, 5× to 100×, 5× to 75×, 5× to 50×, and 5× to 25× that of an individual, nonlinked sulfated GAG. In some embodiments, polymer conjugates of the present invention have a molecular weight in a range of 5× to 25× that of an individual, nonlinked sulfated GAG.

In some embodiments, polymer conjugates of the present invention are soluble in aqueous solution. In some embodiments, a polymer conjugate of the present invention comprises a plurality of sulfated glycosaminoglycan (GAG) polymer chains, wherein each sulfated GAG is linked to one or more sulfated GAG polymer chains via a linker agent, and wherein the polymer conjugate is soluble in aqueous solution and has a molecular weight that is 3× to 100× that of an individual, nonlinked sulfated GAG.

Without wishing to be bound by any particular theory, polymer conjugate variations include but are not limited to varying length, sulfation pattern, molecular weight, chemical composition, and the like. These variations, which may be controlled using the methods provided herein, can affect the conformation, molecular weight, hydrating, mechanical, and cell signaling functions of the polymer conjugate.

Linker Agent

The skilled artisan will be familiar with types of direct linker agents that are appropriate for linking GAG polymers and other polymers used in accordance with the present invention. It will be appreciated that the terms "linking agent" and "linker" are interchangeable, with the understanding that the linker is a portion of the conjugate derived from reaction with a linker agent.

In some embodiments, a linker agent is bifunctional. In some embodiments, the linker agent is not polymeric. In some embodiments, a linker agent is only polymeric where a monomeric unit repeats 10 or fewer times. In some embodiments, a linker agent is only polymeric where a monomeric unit repeats 5 or fewer times. In some embodiments, a linker agent has a molecular weight of less than about 150 Da, 200 Da, 250 Da, 300 Da, 350 Da, 400 Da, 450 Da, 500 Da, 600 Da, 700 Da, 800 Da, 900 Da, or 1000 Da. In some embodiments, a linker agent is not polymeric and is less than about 150 Da, 200 Da, 250 Da, 300 Da, 350 Da, 400 Da, 450 Da, 500 Da, 600 Da, 700 Da, 800 Da, 900 Da, or 1000 Da. In some embodiments, a linker agent is not polymeric and is less than about 1000 Da. In some embodiments, a linker agent is not polymeric and is less than about 500 Da. In some embodiments, a linker agent is not polymeric and is less than about 250 Da. In some embodiments, a linker agent is not polymeric and is less than about 200 Da. In some embodiments, a linker agent is not polymeric and is less than about 150 Da. In some embodiments, a linker agent is not polymeric and is less than 150 Da, 200 Da, 250 Da, 300 Da, 350 Da, 400 Da, 450 Da, 500 Da, 600 Da, 700 Da, 800 Da, 900 Da, or 1000 Da.

In some embodiments, a linker agent is selected from the group consisting of divinylsulfone (DVS), diepoxides, epichlorohydrin (Epi), butanedioldiglycidyl ether (BDDE), and a combination thereof. In some embodiments, a linker agent is epichlorohydrin (Epi). In some embodiments, a linker agent is butanedioldiglycidyl ether (BDDE). In some embodiments, a linker agent is a biscarbodiimide. In some embodiments, a linker agent is phenylene-bis(ethyl carbodiimide). In some embodiments, a linker agent is 1,1'-carbonyldiimidazole. In some embodiments, a linker agent is divinylsulfone (DVS).

In some embodiments, a linker agent is bromoacetic NHS ester, 6-(iodoacetamido)caproic acid NHS ester, maleimidoacetic acid NHS ester, maleimidobenzoic acid NHS ester, or MMCCH (4-(maleimidomethyl) cyclohexane-1-carboxyl hydrazide).

In some embodiments, a linker is a peptidic fragment comprising from 2 to about 20 amino acyl residues, a linear or branched chain alkyl or aryl carboxylic ester, or a Ci-20 saturated or unsaturated, straight or branched, hydrocarbon chain, wherein one or more methylene units of the linker are optionally and independently replaced by cyclopropylene, —CHOH—, —NR—, —N(R)C(O)—, —C(O)N(R)—, —N(R)SO$_2$—, —SO$_2$N(R)—, —O—, —C(O)—, —OC(O)—C(O)O—, —S—, —SO—, —SO$_2$—, —C(=S)—, or —C(=NR)—.

In some embodiments, a linker or linker agent contains a short poly(alkyleneoxide) chain. In some embodiments, a linker or linker agent is a short poly(ethyeneoxide)chain with epoxide groups at both ends, such as poly(ethylene glycol) diglycidyl ether.

Sulfated GAG

In some embodiments, a sulfated GAG for use in accordance with the present invention is selected from the group consisting of chondroitin sulfate, heparan sulfate, dermatan sulfate, keratan sulfate, heparin, and combinations thereof. In some embodiments, a sulfated GAG is chondroitin sulfate. Chondroitin sulfate consists of repeating disaccharide units of N-acetylgalactosamine (GalN) and glucuronic acid (GlcN). In some embodiments, chondroitin sulfate can have over 100 sugars, each of which can be sulfated in variable positions and quantities (e.g., chondroitin sulfate A, C, D, and E). In some embodiments, the molecular weight of a sulfated GAG may be greater than about 1,000 Da, 5,000 Da, 10,000 Da, 15,000 Da, 20,000 Da, 30,000 Da, 40,000 Da, 50,000 Da, 100,000 Da, or a range including any two of these numbers. In some embodiments, the molecular weight of chondroitin sulfate may be greater than about 1,000 Da, 5,000 Da, 10,000 Da, 15,000 Da, 20,000 Da, 30,000 Da, 40,000 Da, 50,000 Da, 100,000 Da, 200,000, Da or a range including any two of these numbers.

Modified GAGs

In some embodiments, polymers conjugates of the present invention can be prepared by using modified GAGs, wherein at least one modifier has been introduced to at least one polymer GAG chain. As described above, GAGs have numerous hydroxyl and carboxyl functionalities along the chain. In addition, the reducing end of the GAG provides a single and unique chemical functionality. In order to extend and enhance the therapeutic benefit of the novel compositions described in this invention, the present invention encompasses the recognition that a modifier may be introduced onto the GAG chains prior to reaction with a linking agent. Practicing the methods of this invention with chemically modified GAGs, or GAG glycoconjugates, will provide high molecular weight proteoglycan mimics with the additional benefits endowed by modifier. For example, a sulfated GAG bearing a peptide with affinity for collagen-I, collagen-II, other collagen isoforms, elastin, integrin receptors, or other ECM components or cell surface proteins including but not limited to galectins will enable more specific binding of the proteoglycan mimic to the target biomolecule. The literature has described several examples of covalent modification of GAGs, and suitable chemistries for such modifications are known to the skilled artisan.

In some embodiments, sulfated GAG may be modified along the GAG polymer chain. In some embodiments, a modifier may be introduced onto a sulfated GAG prior to linking a GAG chain backbone with a linking agent by various methods known to one of skill in the art. In some embodiments, a modifier may be introduced onto a sulfated GAG at its reducing end using reducing end chemistry familiar to the skilled artisan (e.g., reductive amination).

In some embodiments, a sulfated GAG is modified via carboxyl groups along the GAG polymer chain. In some embodiments, a carboxyl group is subjected to peptide coupling conditions to form an amide bond, thereby introducing a modifier. Suitable peptide coupling conditions are well known in the art and include those described in detail in Han et al., Tetrahedron, 60, 2447-67 (2004), and in V R Pattabiraman et. al., Nature, 480, 471-479 (2011), the entirety of which is hereby incorporated by reference. In some embodiments, suitable peptide coupling conditions comprise a peptide coupling reagent selected from a carbodiimide or triazole activating reagent, in the presence of a base such as DIEA or other bases familiar to one skilled in the art. In certain embodiments, the peptide coupling conditions include the addition of HOBt, HOAt, DMAP, BOP, HBTU, HATU, BOMI, DCC, EDC, IBCF, or a combination thereof. In some embodiments, a peptide coupling agent is selected from a triazine activating agent such as 4-(4,6-dimethoxy-1,3,5-triazin-2-yl)-4-methylmorpholinium chloride (DMTMM).

In some embodiments, a soluble high molecular weight sulfated GAG composition may be prepared with polymers that have been chemically substituted with groups to enhance their performance in their intended applications. In some embodiments, such modifiers are substituted randomly along a GAG polysaccharide chain, or only at the reducing end of the chain. In some embodiments, provided polymer conjugates comprise a sulfated GAG such as chondroitin sulfate (ChS) substituted with a peptide modifier known to have strong affinity for a component of the ECM (e.g., collagen, elastin). In other embodiments, provided polymer conjugates comprise a sulfated GAG substituted with an antioxidant modifier or other molecule to enhance its therapeutic benefit. Peptide conjugation is well known in the art as a means of adding biological recognition and function to synthetic polymers and biomaterials. Many short peptide motifs have been identified and utilized in biomaterials applications that can be useful in the formation of GAG conjugates for this invention. Many of these peptides are derived from natural proteins having the desired affinity for a given target biomolecule.

In some embodiments, provided polymer conjugates comprise a sulfated GAG that is substituted with an integrin-binding modifier. Most well-known are the peptide motifs for binding to cell surface integrins are derived from fibronectin: GRGDS (SEQ ID NO: 1), PHSRN (SEQ ID NO: 2), REDV (SEQ ID NO: 3), and LVD. These peptides and their derivatives have affinity for cell surface integrins and have been covalently bound to biomaterials matrices to immobilize cells. Integrin-binding peptides derived from laminin have also been used to attract cells into biomaterials: YIGSR (SEQ ID NO: 4), GIIFFL (SEQ ID NO: 5), IKVAV (SEQ ID NO: 6), their derivatives, and many others.

In some embodiments, provided polymer conjugates comprise a sulfated GAG that is substituted with a collagen-binding agent. There are several peptides known to bind to collagen surfaces. Some have been derived from Decorin: SYIRIADTNITGC (SEQ ID NO: 7) (known as dc-13), LRELHLNNN (SEQ ID NO: 8) (IS-6) and LHERHLNNN (SEQ ID NO: 9). Another well-known collagen-binding peptide is [GPO]7, a 7-mer repeat of the Glycine-Proline-Hydroxyproline collagen motif has helicogenic affinity to fibrillar collagen. The peptide GLRSK-SKKFRRPDIQYPDA (SEQ ID NO: 10) is described in U.S. Pat. No. 9,133,246 B2, where it was used as part of a fusion protein targeted to collagen. U.S. Pat. No. 9,200,039 B2 describes the collagen binding peptide RRANAALKAGE-LYKSILYGC (SEQ ID NO: 11) (known as SILY) and WYRGRLGC (SEQ ID NO: 12) as well as several other examples. In addition, U.S. Pat. No. 8,846,003 B2 describes peptides with specificity for binding at collagen-III surfaces such as: KELNLVYTGC (SEQ ID NO: 13) and GSITTI-DVPWNVGC (SEQ ID NO: 14). Several cyclic peptides with affinity for collagen are described in U.S. Pat. No. 8,034,898 B2 including: WHCYTYFPHHYCVYG (SEQ ID NO: 15); GWHCYTYFPHHYCTYG (SEQ ID NO: 16); AWHCYTYFPHHYCVYG (SEQ ID NO: 17); LWHCYTYFPHHYCVYG (SEQ ID NO: 18); YWHCYTYFPHHYCVYG (SEQ ID NO: 19).

In some embodiments, provided polymer conjugates comprise a sulfated GAG that is substituted with an hyaluronan binding modifier. Peptides with affinity for binding to hyaluronan in the ECM are described in U.S. Pat. No. 9,200,039 B2. These include GAHWQFNALTVRGGGC (SEQ ID NO: 20) (known as GAH) and other examples.

Preferably, polymer conjugates in accordance with the invention comprise at least one sulfated GAG polymer chain that is substituted with at least one glycan ligand for galectins, for example a sulfated GAG polymer chain comprising at least one β-galactose residue (e.g. β-galactoside).

In some embodiments, a provided polymer conjugate comprises any of the above-described peptides or glycans as a modifier.

Additional Polymers

In some embodiments of provided polymer conjugates, sulfated GAGs are directly conjugated with other polymers and biomolecules. In some embodiments, hyaluronic acid (HA) or carboxymethyl cellulose (CMC) are incorporated to form a hybrid high molecular weight soluble polymer composition. In some embodiments, sulfated GAGs may be directly conjugated together with other polymers and biopolymers with molecular weights greater than about 250 kDa, 300 kDa, 350 kDa, 400 kDa, 450 kDa, 500 kDa, 1,000 kDa, or a range including any two of these numbers. Exemplary such conjugates are described in further detail below.

Methods of Preparing GAG Polymer Conjugates

As described above, polymer conjugates of the invention are synthesized by an appropriate selection of synthetic reagents and methods. The discussion below is offered to illustrate certain of the diverse methods available for use in assembling the polymer conjugates of the invention. However, the discussion is not intended to limit the scope of reactions or reaction sequences that are useful in preparing the compounds of the present invention.

Scheme A as illustrated below depicts a sulfated GAG (e.g., chondroitin sulfate) and various locations in which a linker agent (e.g., DVS) may be attached:

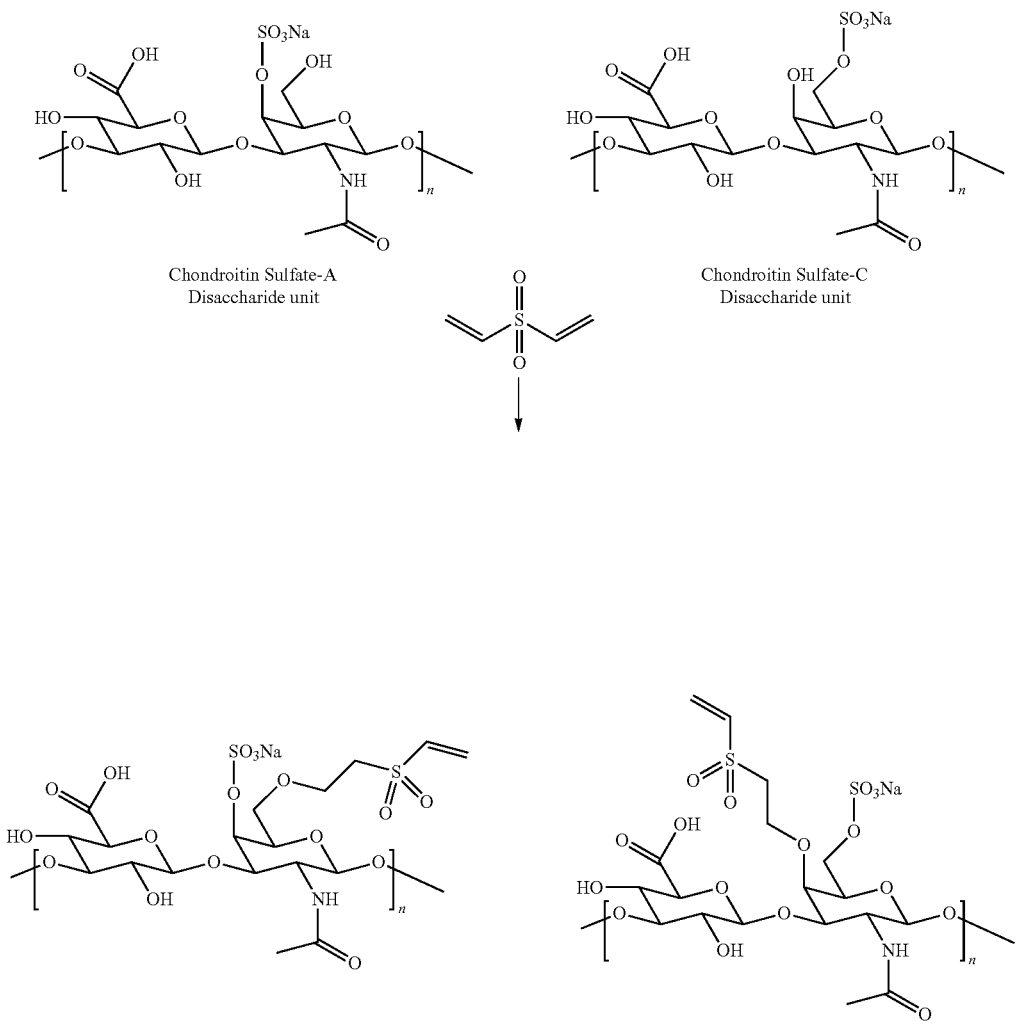

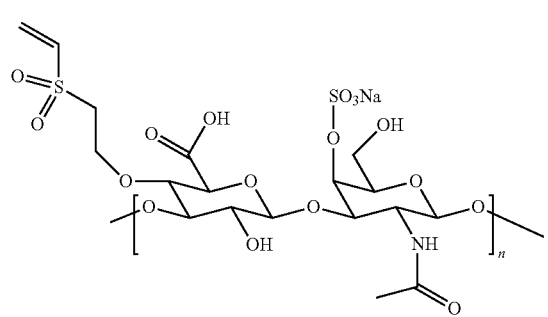
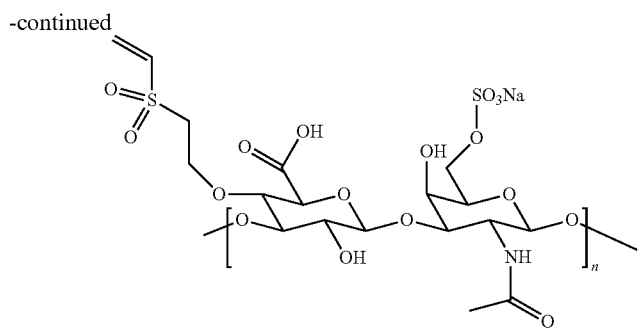
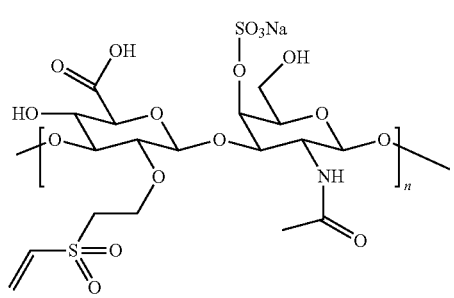
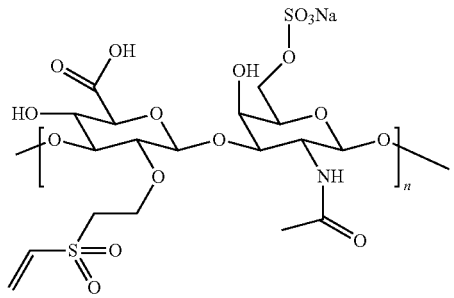
Scheme B as illustrated below depicts an example of a sulfated GAG reacted with a second sulfated GAG with a bound linker agent (DVS) to form a polymer conjugate:
Scheme B
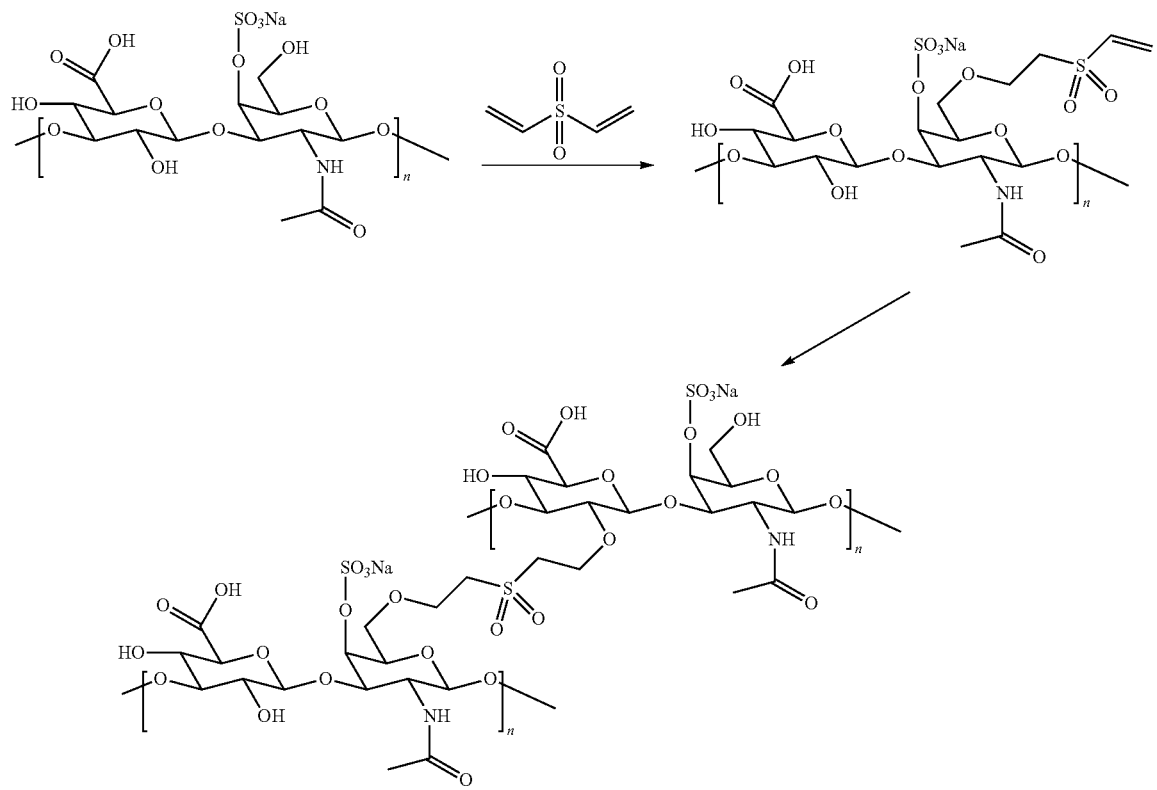

Applicant has observed that, under conditions where the sulfated GAG is present in high concentration, a strong clear gel may be formed rapidly. For example, using a commercial bovine sourced chondroitin sulfate material of Mw=14,000 Da, a hydrogel can be formed within 1-2 hours after addition of DVS in 0.1 N NaOH solution when the chondroitin sulfate is at concentrations greater than 8 wt % (8 g polymer contained in 100 g of solution) and sufficient DVS is used.

Figure 5:
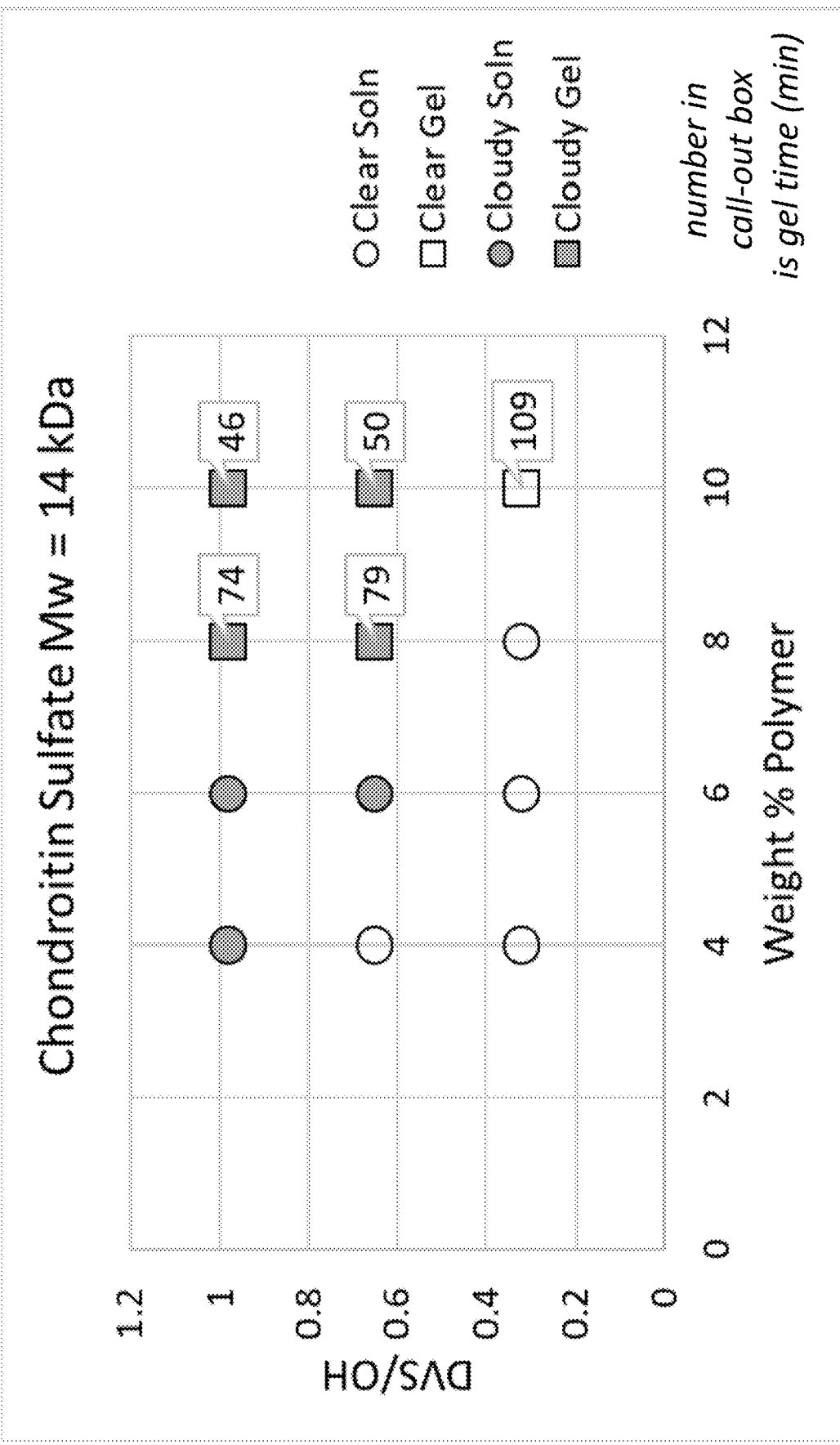
FIG. 5 depicts a plot of [DVS]/OH vs. polymer wt % for chondroitin sulfate of Mw=14 kDa noting conditions where gel formation and/or loss of solubility is observed.
Figure 6:
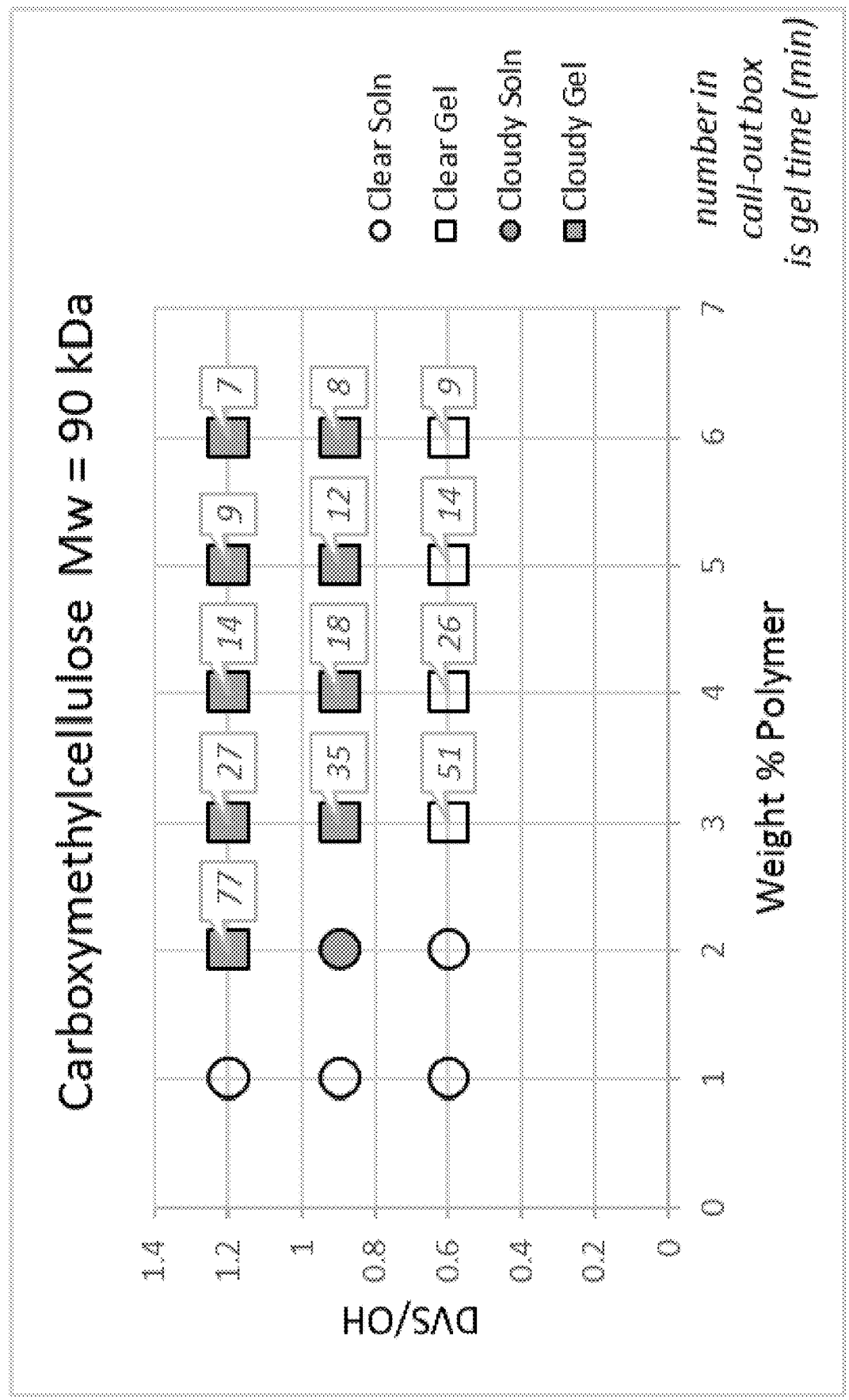
FIG. 6 depicts a plot od [DVS]/OH vs. polymer wt % for carboxymethylcellulose Mw=90 kDa noting conditions where gel formation and/or loss of solubility is observed.

FIGS. 5 and 6 illustrate various combinations of the DVS/OH ratio and polymer concentration expressed as the weight % of polymer in solution. These figures show that in some combinations, gels are formed and in others gels are not formed. In addition, the approximate time required to form a gel is included in the figure, and it is possible to quench such a reaction prior to formation of a gel. FIGS. 5 and 6 also indicate conditions in which the reaction mixture remains clear, and conditions in which the reaction becomes hazy or opaque due to the formation of an insoluble, heavily modified polymer derivative.

The present invention provides, among other things, methods for preparing polymer conjugates where the predominant product is a sulfated GAG polymer conjugate soluble in aqueous solution. According to one aspect of the present invention, a sulfated GAG is used in methods provided herein at a concentration selected to avoid formation of a gel.

In some embodiments, a sulfated GAG is at concentrations greater than about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, or a range including any two of these numbers. In some embodiments, a sulfated GAG is at a concentration between the range of 2 wt % and 20 wt %, 2 wt % and 18 wt %, 2 wt % and 16 wt %, 2 wt % and 14 wt %, 2 wt % and 12 wt %, 2 wt % and 10 wt %, 4 wt % and 20 wt %, 6 wt % and 20 wt %, 8 wt % and 20 wt %, 10 wt % and 20 wt %, 5 wt % and 15 wt %, 5 wt % and 10 wt %, 8 wt % and 16 wt %, and 8 wt % and 12 wt %. In some embodiments, chondroitin sulfate (ChS) is used at concentrations greater than about 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, 20 wt %, or a range including any two of these numbers.

In some embodiments, experiments run in the range between about 8 wt %-16 wt % ChS reveal that the speed of gel formation increases with both the concentration of ChS and the amount of DVS used. For example, when the mole ratio of DVS/hydroxyl group equivalents available on the biopolymer is less than 0.1, a gel is not formed after 90 minutes even for higher concentration solutions (10-12 wt %) of ChS.

In some embodiments, when these reactions were carried out under conditions where the DVS/hydroxyl ratio was systematically increased, it was observed that the speed of gel formation was hastened. Moreover, it was found that when the DVS/hydroxyl levels were high (near or above 1.0), some reactions became cloudy or even formed a white solid precipitate. Characterization of this insoluble product by NMR spectroscopy and found it to be a chondroitin sulfate derivative highly substituted with vinyl sulfone groups.

"Branched" Polymer Conjugates

Figure 2:
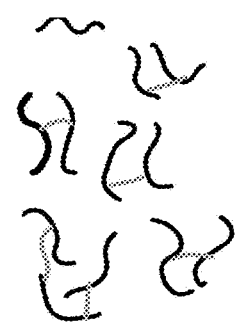
FIG. 2 is a schematic showing the formation of soluble branched polymer chains.
Figure 2:
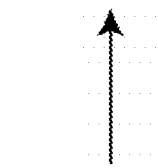
Figure 2:
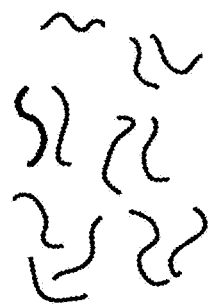

In some embodiments, a polymer conjugate of the present invention has branched architecture. See, for example, FIG. 2. In some embodiments, a sulfated GAG is reacted with a linking agent under conditions where the GAG concentration and the molar ratio of linking agent to GAG have been selected to provide a soluble branched polymer rather than an extended crosslinked network. In some embodiments, a linker agent is DVS and the DVS/hydroxyl ratio is between the range of about 0.01 to 0.6. In some embodiments, the DVS/hydroxyl ratio is 0.01, 0.05, 0.1, 0.2, 0.3, 0.4, 0.5, 0.6, or a range including any two of these numbers.

In certain embodiments, the present invention provides a method of preparing polymer conjugates comprising the steps of: i) providing sulfated GAG in aqueous solution at a concentration of about 2 wt %-20 wt %; and ii) contacting the sulfated GAG with a linking agent, wherein the molar ratio of GAG hydroxyl groups to linking agent is less than that required for gel formation to form a soluble branched polymer. In some embodiments, a sulfated GAG in step i has a molecular weight from 10,000 Da to 100,000 Da. In some embodiments, the molar ratio of GAG hydroxyl groups to linking agent (e.g., DVS/hydroxyl ratio) is from 0.01 to 0.6.

In some embodiments, a sulfated GAG is reacted with a direct linking agent under conditions where the reaction can be terminated before an extended crosslinked network is formed. In these cases, the linking reaction is easily terminated by the addition of acid (such as HCl) to bring the pH down to a neutral value. Again a soluble branched polymer is obtained rather than an extended crosslinked network. In some embodiments, the reaction occurs for a certain amount of time before the reaction is terminated. In some embodiments, the reaction occurs for about 1 to 120 minutes. In some embodiments, the reaction occurs for about 25-40 minutes. In some embodiments, the reaction occurs for about 40 minutes. In some embodiments, the reaction occurs for about 90 minutes.

In some embodiments, a branched polymer conjugate has a molecular weight greater than about 15,000 Da, 20,000 Da, 30,000 Da, 40,000 Da, 50,000 Da, 100,000 Da, 200,000 Da, 300,000 Da, 400,000 Da, 500,000 Da, 1,000,000 Da, or a range including any two of these numbers.

"Bottlebrush-Like" Polymer Conjugates

Figure 3:
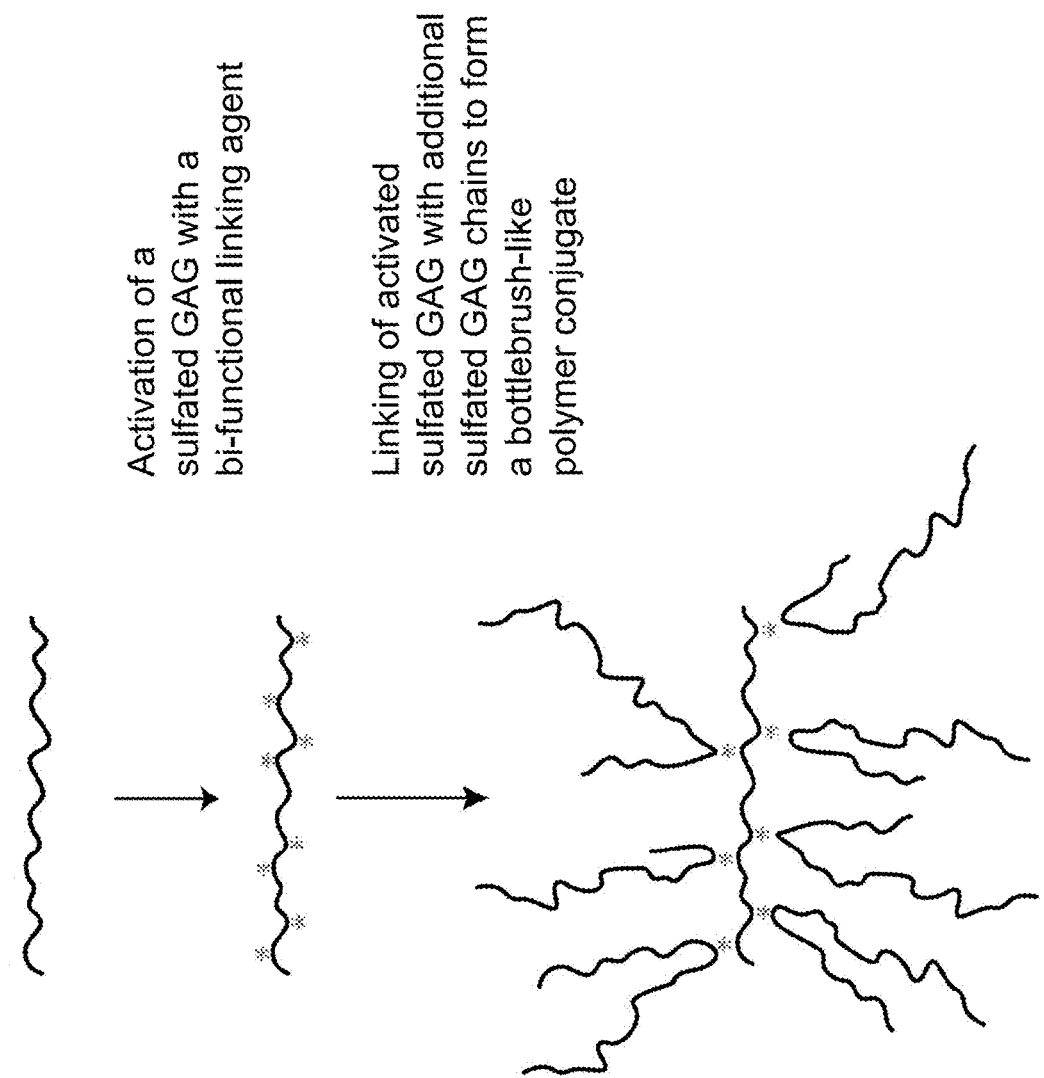
FIG. 3 depicts activation of a sulfated GAG with a bifunctional linking agent following by linking of the activated sulfated GAG with additional sulfated GAG chains to form a bottlebrush-like polymer conjugate.
Figure 4:
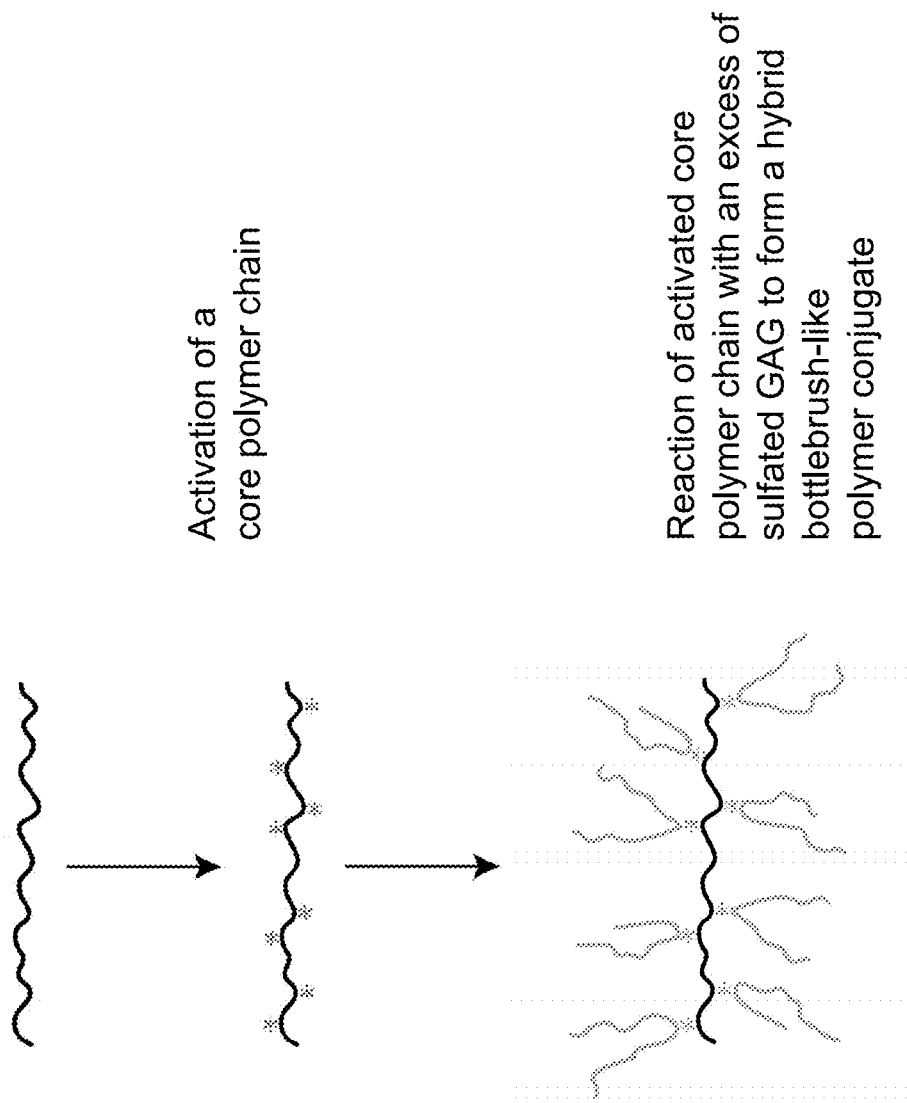
FIG. 4 depicts activation of a core polymer chain with a bifunctional linking agent followed by reaction of the activated core polymer chain with an excess of a sulfated GAG to form a hybrid bottlebrush-like polymer conjugate (i.e., wherein the core polymer chain is not a sulfated GAG).

In some embodiments, a polymer conjugate of the present invention has bottlebrush-like architecture. See, for example, FIG. 3. In some embodiments, a sulfated GAG is reacted with a linking agent under conditions where reactants are sequentially introduced. In some embodiments, this staged addition of reactants significantly affects the molecular architecture and properties of the product. For example, in a 1-pot procedure, a small portion of a sulfated GAG can be activated with a linking agent in dilute solution to form an intermediate multivalent reactive core polymer. Subsequent addition of an excess of the same or different sulfated GAG results in formation of a soluble, high molecular weight sulfated GAG composition with a bottlebrush-like architecture.

Thus, in some embodiments the present invention provides a method of preparing polymer conjugates via sequential introduction of the sulfated GAG in a single reaction, comprising the steps of: i) providing a sulfated GAG; and ii) reacting the sulfated GAG with a linking agent under conditions where a small portion of the sulfated GAG is reacted with the full portion of linking agent; and iii) adding the remaining portion of sulfated GAG to form a soluble conjugate with bottlebrush-like architecture.

In some embodiments, a high molecular weight core polymer capable of direct reaction with a linking agent (e.g., CMC, HA) is reacted in the initial step of the 2-stage synthetic procedure. A sulfated GAG may then be introduced to react with the modified core polymer forming a bottlebrush-like polymeric composition in a 1-pot procedure.

In some embodiments, the present invention provides a method of preparing polymer conjugates comprising the steps of: i) activating a core polymer with a linking agent in dilute solution to form an intermediate multivalent reactive core polymer; and ii) adding an excess of a sulfated GAG to form a soluble bottlebrush-like polymer. In certain embodiments, step i comprises activating a core polymer with a linking agent under conditions where a small portion of the core polymer is reacted with the full portion of linking agent. In certain embodiments, step i comprises activating a substoichiometric amount of a core polymer (i.e., an excess of linking agent over polymer hydroxyl groups) with a linking agent in dilute solution to form an intermediate multivalent reactive core polymer. In some embodiments, the core polymer of step i is a sulfated GAG identical to that added in step ii. In some embodiments, the core polymer of step i is a sulfated GAG different from that added in step ii. In some embodiments, the core polymer of step i is not a sulfated GAG. In certain embodiments, the core polymer in step i is carboxymethylcellulose. In certain embodiments, the core polymer in step i is hyaluronic acid.

In some embodiments, a provided polymer conjugate is prepared in a 2-step reaction in which the core polymer is first functionalized with a linking agent in dilute solution, and is then isolated by precipitation or other means. The intermediate core polymer modified with the linking agent can be characterized and/or purified. Subsequent reaction of this intermediate core polymer in a second reaction with a sulfated GAG in concentrated solution provides a soluble bottlebrush-like polymeric composition.

Thus, in some embodiments, the present invention provides a method of preparing polymer conjugates comprising the steps of: i) functionalizing a core polymer with a linking agent in dilute solution to form an intermediate core polymer; ii) isolating the intermediate core polymer; and iii) reacting the intermediate core polymer with a sulfated GAG in concentrated solution to form a soluble bottlebrush-like polymer.

In some embodiments, a bottlebrush-like polymer conjugate has a molecular weight greater than about 15,000 Da, 20,000 Da, 30,000 Da, 40,000 Da, 50,000 Da, 100,000 Da, 200,000 Da, 300,000 Da, 400,000 Da, 500,000 Da, 1,000,000 Da, 2,000,000 Da or a range including any two of these numbers.

Characterization Techniques

As described above, in some embodiments polymer conjugates of the present invention are soluble in aqueous solution. Such conjugates are in contrast to known GAG polymer conjugates that are gels having extended crosslinked networks. While the skilled person can differentiate between materials that are gels and those that are not gels, for the avoidance of doubt, it is noted that for polymerization in homogeneous solution, the formation of an extended crosslinked network will be characterized by a loss of solution characteristics. For example, the reaction mixture will no longer flow, and when the gel is added to a large volume of water it may swell, but it will not dissolve. Such gels take on the properties of a solid, or viscoelastic material. In addition, such gels have viscoelastic properties that can be quantified using rheometry. For example, many strong gels have a storage modulus (G') that is greater than its loss modulus (G").

In some embodiments, provided polymer conjugates will maintain solution flow properties when dissolved in water.

In some embodiments, provided polymer conjugates will have molecular weight distributions and degree of branching that will be characteristic of the method of synthesis, and will be reproducible from batch to batch. In some embodiments, provided polymer conjugates are characterized in that a clear viscous fluid, and not a gel, is observed during manufacture of provided polymer conjugates. In some embodiments, polymer conjugates are a clear viscous fluid in aqueous solution.

Characterization of provided polymer conjugates may be provided by gel permeation chromatography (GPC) and dynamic light scattering (DLS). In some embodiments, parameters related to flow such as viscosity or modulus may be determined by viscometry and rheology.

Hydrodynamic radius (Rh) is determined by DLS and is directly related to molecular weight and architecture (type/degree of branching). In some embodiments, an enhancement or increase of Rh over that of the starting material will be achieved. In some embodiments, polymer conjugates of the present invention will have an increased hydrodynamic radius compared to that of a reference. In some embodiments, aggrecan may be a reference used to model an upper limit for both molecular weight and Rh. In some embodiments, starting material (e.g., non-linked sulfated GAG) may be used as a reference.

DLS is a convenient method for direct determination of the size of polymers in solution (Rh), however it does not directly measure molecular weight. Knowing the hydrodynamic radius allows for estimation of molecular weight. DYMANICS® software (Wyatt technologies) uses a shape model to estimate Mw from Rh. This calculation can be done after input of a general polymer architecture model: globular, coiled, branched.

Purification of Polymer Conjugates

In some embodiments, polymer conjugates may be purified by methods known to those of skill in the art. In some embodiments, polymer conjugates may be purified by dialysis. In some embodiments, polymer conjugates may be purified by tangential flow filtration. In some embodiments, polymer conjugates may be precipitated from a crude reaction product. In some cases, the polymer conjugates may be precipitated from the reaction mixture, collected, redissolved in water and precipitated again. Several redissolution/precipitation cycles may be performed.

Methods of Use

Injuries to soft tissue, for example, vascular, skin, or musculoskeletal tissue, are quite common. Surgical approaches to correct soft tissue defects and or damage in the body generally involve the implantation of structures made of biocompatible, inert materials that attempt to replace or substitute for the defective function. Implantation of nonbiodegradable materials results in permanent structures that remain in the body as a foreign object. Implants that are made of resorbable materials are suggested for use as temporary replacements where the object is to allow the healing process to replace the resorbed material. However, these approaches have met with limited success for the long-term correction of structures in the body.

As a person ages, facial rhytids (wrinkles) and folds develop in response to the loss of facial fat and the decrease of the skin elasticity. The skin loses shape and acute wounds take longer to heal and scar more easily. Physicians have over the years tried various methods and materials to combat the facial volume loss of the soft tissue of the face. Scientists and physicians are constantly searching for the ideal dermal filler.

Soft tissue conditions further include, for example, conditions of skin (e.g., scar revision or the treatment of traumatic wounds, severe burns, skin ulcers (e.g., decubitus (pressure) ulcers, venous ulcers, and diabetic ulcers), and surgical wounds such as those associated with the excision of skin cancers); vascular condition (e.g., vascular disease such as peripheral arterial disease, abdominal aortic aneurysm, carotid disease, and venous disease; vascular injury; improper vascular development); conditions affecting vocal cords; cosmetic conditions (e.g., those involving repair, augmentation, or beautification); muscle diseases; conditions of connective tissues such as tendons and ligaments, including but not limited to a periodontal ligament and anterior cruciate ligament; and conditions of organs and/or fascia (e.g., the bladder, intestine, pelvic floor).

Degenerated and damaged soft tissues of the musculoskeletal system cause and increase the risk of medical complications resulting in intense pain and restricted motion. For example, degenerated and damaged soft tissues of the spine represent the major source of back pain for millions of people around the world. Soft tissue degeneration of the ligaments and intervertebral discs also increase the risk of damage to and back pain from local spinal joints, including: zygapophysical (facet), costovertebral, sacroiliac, sacral vertebral and atlantoaxial joints. In some embodiments, polymer conjugates of the present invention are for use in medicine. In some embodiments, polymer conjugates of the present invention are for use in treating a disease, disorder, or condition associated with a soft tissue in a mammal. In some embodiments, polymer conjugates of the present invention are for use in treating diseases, disorders, or conditions associated with soft tissue defects and/or disorders, where administration of a conjugate of the present invention to the soft tissue site results in functional restoration of the soft tissue, in whole or in part.

In some embodiments, soft tissue treated in accordance with the present invention is selected from the group consisting of intervertebral disc, skin, heart valve, articular cartilage, cartilage, meniscus, fatty tissue, craniofacial, ocular, tendon, ligament, fascia, fibrous tissue, synovial membrane, muscle, nerves, blood vessel, and any combination thereof. In some embodiments, polymer conjugates of the present invention are for use in dermal, orthopedic, urology, wound repair, and topical cosmetics.

In some embodiments, polymer conjugates of the present invention are for use in treating a disease, disorder, or condition associated with degradation of the ECM in a mammal. In some embodiments, polymer conjugates of the present invention are for use in treating diseases, disorders, or conditions associated with ECM defects and/or disorders, where administration of a conjugate of the present invention to the ECM results in functional restoration of the ECM, in whole or in part.

In some embodiments, polymer conjugates of the present invention provide a method of delaying the onset of (e.g., preventing) soft tissue loss. In some embodiments, polymer conjugates of the present invention provide a method for augmenting soft tissue. In some embodiments, polymer conjugates of the present invention provide a method for cosmetic augmentation. In some embodiments, polymer conjugates of the present invention provide methods of treating a subject suffering from age related degeneration of connective tissues or diseases related to the degeneration of connective tissues.

In some embodiments, polymer conjugates of the present invention are for use in acute wound healing. In some embodiments, polymer conjugates of the present invention are for use in regenerative medicine.

Interstitial cystitis (IC), or bladder pain syndrome (BPS), is a chronic disease affecting 4 to 12 million people in the United States, mostly women. IC/BPS is characterized by frequent urination, increased urgency, and pain associated with bladder filling. Therefore, polymer conjugates of the present invention are preferably for use in treating the damaged urothelium of the bladder found in patients suffering from painful bladder syndrome or interstitial cystitis. In some embodiments, the polymer is preferably administered to the bladder via intravesical instillation.

Although the etiology is unknown, and without being limited to any particular theory, one leading theory proposes that bladder pain symptoms originate from a loss of the tight impermeable barrier at the luminal bladder surface leading to activation of visceral afferent fibers innervating the urothelium. The "umbrella cells" that comprise the luminal cell layer responsible for bladder impermeability can be absent or less than fully differentiated, the normal layer of glycosaminoglycans (GAGs) on the surface is compromised and tight junction protein expression is altered. Parsons demonstrated that IC patients showed a significantly higher absorption of urea instilled into the bladder than did controls, and Hurst showed unambiguously using MRI that the urothelium of IC/BPS patients have significantly greater permeability than normal controls. What is unclear is how the bladder loses its impermeability. Evidence suggests it can occur both endogenously through neural connections, possibly modulated by inflammatory cells, and from substances in the urine or loss of cation scavengers.

Therapeutic options for IC/BPS are limited despite the wide variety of agents that have been tried. Some success has come through the restoration of urothelial impermeability through GAG-replenishment therapy (30-32). GAG-replenishment involves intravesicular administration of chondroitin sulfate and hyaluronan, either singly or together, heparin, or pentosan polysulfate (ELMIRON®). Unfortunately, response rates rarely exceed 50% to 60%. The limited efficacy of current GAG-replacement therapy may be explained by the inability of these agents to replicate the native GAG layer of the urothelium. The urothelial GAG layer is composed of proteoglycans (PGs), mostly biglycan and perlecan. PGs are glycoproteins usually substituted with clusters of sulfated GAG chains, thereby increasing the interactions of these sulfated GAGs with other biomolecules and creating a zone of very high anionic charge. The resulting osmotic pressure ensures very effective hydration for PG-rich tissues and interfaces. Current approaches for GAG-replenishment in IC/BPS provide only linear, single-chain GAGs such as hyaluronic acid, which is non-sulfated, or sulfated GAGs of low MW (<50 kDa) such as chondroitin sulfate. These single chain GAGs are not able to mimic the clustered sulfated GAG environment provided by PGs on the surface of the native urothelium. PGs themselves are not practical therapeutics because they are complex biomolecules difficult to isolate and purify from tissue.

However, the proteoglycan mimic conjugated polymers of the present invention mimic the PG structure by representing a polyvalent array of sulfated GAG chains for binding biological surfaces in a way that is not possible for single, linear GAG chains. For restoring bladder impermeability in IC/BPS, binding to the bladder endothelium is critical, and therefore this polyvalent display of sulfated GAG chains presented by proteoglycan mimic conjugated polymers of the invention represents a significant innovation. Preferably, the proteoglycan mimics of the invention provide targeted treatment of IC/BPS by further functionalization with, for example a glycan ligand for galectin, such as a ligand comprising a β-galactoside. Such polymer conjugates "decorated" with, for example β-galactoside will target galectins present in the bladder epithelium. Therefore, the invention provides method of treating Interstitial Cystitis (IC) in a patient comprising the step of administering to the patient, a polymer conjugate of the invention, and preferably a polymer conjugate of the invention wherein at least one sulfated GAG polymer chain comprises at least one glycan ligand for galectin (e.g., a β-galactoside).

In some embodiments, polymer conjugates of the present invention are for use in treating a degenerated disc. In some embodiments, polymer conjugates of the present invention are for use in a method of administering polymer conjugates into the nucleus of a degenerated disc in order to increase the osmotic potential of the disc. Administration of a material of polymer conjugates into the nucleus of a degenerated disc can restore normal disc height and function. Preferably a polymer conjugate of the invention is administered by direct injection into an intervertebral disc. Such administration can result in whole or partial restoration of the load-bearing and viscoelastic properties of the defective intervertebral disc.

In some embodiments, polymer conjugates of the present invention are for use in osteoarthritis OA of the knee and other joints. OA, also known as degenerative joint disease, is the most common form of arthritis and results from the gradual breakdown of cartilage that accompanies aging. Typically, OA follows trauma or chronic joint injury due to some other type of arthritis such as rheumatoid arthritis. Alternatively, OA can result from overuse of a particular joint. OA most commonly involves the joints of the elbow, fingers, hips, knees, shoulder, wrist, spine, and toes. Clinically, OA is characterized by joint pain, tenderness, limitation of movement, crepitus, and inexorably progressive disability. It can be present in just one of these joints or in all of them. Although most body tissues can make repairs following an injury, it is believed cartilage repair is hampered by a limited blood supply and the lack of an effective mechanism for cartilage re-growth. Preferably, the invention provides methods of administering the polymer conjugates of the invention to a patient suffering from OA. Preferably, the polymer conjugates of the invention may be administered to the patient by direct injection to the afflicted joint. Preferably, the polymer conjugates of the invention may be administered to the patient by direct injection to the afflicted joint in combination with additional viscosupplementation including but not limited to hyaluronic acid (HA)-containing viscosupplements such as EUFLEXXA®, HYALGAN®, ORTHOVISC®, SUPARTZ®, and SYNVISC®.

The polymer conjugates of the present invention can be used in conjunction with any known or heretofore unknown method of treating a disc disease or condition in a mammal. Preferably, the subject is a human.

Administration

In some embodiments, polymer conjugates of the present invention may be formulated with one or more excipients, buffers, carriers, stabilizers, preservatives and/or bulking agents. In some embodiments, polymer conjugates of the present invention may be formulated using excipients that are fully biocompatible (i.e. non-toxic). In some embodiments, polymer conjugates of the present invention may be formulated using excipients and are buffered at physiological pH by salts (e.g., sodium phosphate salts).

Polymer conjugates of the present invention may be administered to a soft tissue site in a subject, for the functional restoration thereof, using a variety of methods and in a variety of formulations known in the art. The methods of administration are chosen depending on the condition being treated and the pharmaceutical composition. Administration of polymer conjugates of the invention can be done in a variety of ways, including, but not limited to, cutaneously, subcutaneously, intravenously, orally, topically, transdermally, intraperitoneally, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the polymer conjugates of the invention may be through a single route or concurrently by several routes. For instance, oral administration can be accompanied by intravenous or parenteral injections.

Preferably, the subject compositions are administered by intravesical instillation. The procedure generally involves inserting a catheter into urinary tract and filling the bladder with a suitable diluent containing the subject composition. Filling may be made by manual infusion or renal pump. Electromotive drug administration can further assist intravesical drug delivery (see for example, Riedl, C. R. et al., *J. Endourol.* 12: 269-72 (1998); incorporated by reference).

Preferably, the conjugates of the invention are administered by direct injection into the dermis using a small gauge needle or microneedle or microneedle array. The polymer conjugates of the invention as branched biopolymers have the advantage of low viscosity when in solution which facilitates injection through small gauge needles.

In some embodiments, it is preferable that the polymer conjugates of the present invention do not appreciably degrade following administration. In some embodiments, it is preferred that the composition of the invention degrades either rapidly, or slowly, in the tissue. Thus, when administered in the body, polymer conjugates, may be permanent, may be degraded enzymatically, or may be degraded in the presence of a solvent, such as, for example, water.

The methods of the present invention include the determination of optimum doses of the compounds and pharmaceutical compositions for treating IC symptoms, which may be determined in consideration of the results of animal experiments. More specific doses obviously vary depending on the administration method, the condition of the subject such as age, body weight, sex, sensitivity, food eaten, dosage intervals, medicines administered in combination, and the seriousness and degree of the IC. The optimal dose and the administration frequency under a given condition must be determined by the appropriate dosage test of a medical specialist based on these guidelines, and does not constitute undue experimentation for one skilled in the art.

The polymer conjugates of the invention may also be administered using sustained release or long-term delivery methods, which are well known to those skilled in the art. By "sustained release or" "long term release" as used herein is meant that the delivery system administers a pharmaceutically therapeutic amount of polymer conjugate for more than a day, preferably more than a week, and most preferable at least about 30 days to 60 days, or longer. Long term release systems may comprise implantable solids or gels containing the polymer conjugate, such as biodegradable polymers.

The polymer conjugate of the invention may be administered in combination with one or more other drugs (or as any combination thereof). The polymer conjugate of the invention may be usefully combined with another pharmacologically active compound, or with two or more other pharmacologically active compounds, for the treatment of a pain and/or a lower urinary tract symptom (LUTS) associated with IC and/or painful bladder syndrome and/or bladder pain syndrome. For example, the polymer conjugate of the invention may be administered simultaneously, sequentially or separately, in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butalbital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, terazosin, indoramin, alfuzosin, silodosin or 4-amino-6,7-dimethoxy-2-(5-methane-sulfonamido-1,2,3,4-tetrahydroisoquinol-2-yl)-5-(2-pyridyl)quinazoline; prazosin;

a tricyclic antidepressant, e.g. desipramine, imipramine, amitriptyline or nortriptyline; an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, fesoterodine, 5-hydroxymethyltolterodine, propiverine, trospium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular acetaminophen/paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, MIRAXION® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist (eg pizotifen), and particularly a $5-HT_{1B/1D}$ agonist such as eletriptan, sumatriptan, naratriptan, zolmitriptan or rizatriptan;

a $5-HT_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol (trade mark);

a PDE-5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2'1',1:6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5a)(3-amino-methyl-bicyclo[3.2.0]hept-3-yl)-acetic acid, (3 S,5R)-3-aminomethyl-5-methyl-heptanoic acid, (3 S,5R)-3-amino-5-methyl-heptanoic acid, (3 S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3 S,4S)-(1-aminomethyl-3,4-dimethyl-cyclopentyl)-acetic acid, (3 S,5R)-3-amino-5-methyl-nonanoic acid, (3R,4R,5R)-3-amino-4,5-dimethyl-heptanoic acid and (3R,4R,5R)-3-amino-4,5-dimethyl-octanoic acid; (3S,5R)-3-aminomethyl-5-methyloctanoic acid;

a cannabinoid;

metabotropic glutamate subtype 1 receptor (mGluR1) antagonist;

a serotonin reuptake inhibitor such as sertraline, sertraline metabolite desmethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (VIVALAN®), especially a selective noradrenaline reuptake inhibitor such as reboxetine, in particular (S, S)-reboxetine; a dual serotonin-noradrenaline reuptake inhibitor, such as venlafaxine, venlafaxine metabolite 0-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethy]-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c] pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl]phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine; or bupivicaine a 5-HT3 antagonist, such as ondansetron;

glycosaminoglycan layer replacer and anti-inflammatory, such as pentosan polysulphate (Elmiron—trade mark);

a beta-3 agonist, such as YM-178 (mirabegron or 2-amino-N-[4-[2-[[(2R)-2-hydroxy-2-phenylethyl] amino]ethyl]phenyl]-4-thiazoleacetamide), solabegron, KUC-7483 (ritobegron or 2-[4-[2-[[(1S,2R)-2-hydroxy-2-(4-hydroxyphenyl)-1-methylethyl]amino] ethyl]-2,5-dimethylphenoxy]-acetic acid) or AK-134;

an anti-histamine, such as hydroxyzine;

a $H_2$-antagonist, such as cimetidine; or ranitidine silver nitrate;

a steroid;

doxorubicin;

chondroitin sulphate;

disodium chromoglycate;

oxychlorosene (Clorpactin—trade mark); and an immunosuppressant, such as cyclosporine.

EXAMPLES

The examples below are meant to illustrate certain embodiments of the invention, and not to limit the scope of the invention.

Materials and Methods

Chondroitin sulfate was obtained from Bioiberica, EP Injectable grade (GPC data from supplier: Mn=11,400, Mw=13,700 Da, PDI=1.21). The equivalent weight of the disodium chondroitin sulfate-A structural repeat unit is 503.35 g/equiv. ($C_{14}H_{19}O_{14}SNa_2$), and the hydroxyl equivalent weight is 503.35/3=167.78 g/OH equiv. Divinylsulfone 99% was purchased from ACROS Organics. Carboxymethylcellulose (MW=250 kDa, and 90 kDa, degree of substitution=0.80, 226.16 g/equiv., 113.08 g/OH equivalent) was purchased from Sigma Aldrich.

Protocol for DLS

Dynamic light scattering analysis was performed on a DynaPro Nanostar instrument (Wyatt Technology) using Wyatt's Cyclic Olefin Copolymer disposable micro cuvette. Data were collected at 25° C. with an acquisition time of 10 s and the hydrodynamic radii were averaged over 20 acquisitions. Data were fitted using the DYNAMICS software version 7.5 (Wyatt Technology) to obtain hydrodynamic radius and estimate molar mass.

Example 1. Synthesis of a Soluble High MW Chondroitin Sulfate Composition by Direct Reaction with DVS Under Conditions where No Gel is Formed Sodium Chondroitin Sulfate (0.34 g, 2.0 mmol equiv. hydroxyl groups) was dissolved in 2.25 mL DI water in an 8 mL reaction vessel. A clear colorless solution was obtained. DVS (0.034 g, 30 uL, 0.28 mmol) was added volumetrically with a microliter pipette. After gentle mixing, the solution was clear and colorless. Reaction was initiated by the addition of 0.25 mL of 1.0 N NaOH using a microliter pipette. With the addition of NaOH the solution immediately became pale yellow in color and remained clear. The reaction is 12 wt % in chondroitin sulfate and is 0.1M in NaOH (approx. pH 13). The reaction was gently mixed on a rotisserie. It remained fluid and clear over time. Under these reaction conditions (12 wt % polymer, DVS/hydroxyl=0.14) no gel formation was observed over a period of >1 hour. The reaction was quenched 40 minutes after initiation by the addition of 0.25 mL of 1.0 N HCl. The pH after neutralization was found to be approx. 5.0. The reaction solution was diluted with PBS to a total volume of 25 mL.

The diluted reaction solution was analyzed using dynamic light scattering and compared to a control sample from a null reaction identical in all respects except for the omission of DVS. The following hydrodynamic radii and Mw values were found (Table 1):

TABLE 1

| SAMPLE | Hydrodynamic Radius | Mw |
|---|---|---|
| Example 1 | 4.38 nm | 53 kDa |
| Null Reaction Comparator | 2.89 nm | 21 kDa |

Example 2. Synthesis of a Soluble High MW Chondroitin Sulfate Composition by Direct Reaction with DVS with Quenching Prior to Gel Formation Sodium Chondroitin Sulfate (0.34 g, 2.0 mmol equiv. hydroxyl groups) was dissolved in 2.25 mL DI water in an 8 mL reaction vessel. A clear colorless solution was obtained. DVS (0.067 g, 60 uL, 0.57 mmol) was added volumetrically with a microliter pipette. After gentle mixing, the solution was clear and colorless. Reaction was initiated by the addition of 0.25 mL of 1.0 N NaOH using a microliter pipette. With the addition of NaOH the solution immediately became pale yellow in color and remained clear. The reaction is 12 wt % in chondroitin sulfate, DVS/hydroxyl=0.28, and is 0.1M in NaOH (pH 13). The reaction was gently mixed on a rotisserie. It became more viscous over time and remained clear. At 40 minutes after the initiation of reaction, a rapid viscosity build was observed and the reaction was quenched just prior to gelation by the addition of 0.25 mL of 1.0 N HCl. The pH after neutralization was found to be approx. 5.0. The viscous reaction solution was diluted with PBS to a total volume of 25 mL.

The diluted reaction solution was analyzed using dynamic light scattering and compared to a control sample from a null reaction identical in all respects except for the omission of DVS. The following hydrodynamic radii and Mw values were found (Table 2):

TABLE 2

| SAMPLE | Hydrodynamic Radius | Mw |
|---|---|---|
| Example 2 | 6.72 nm | 139 kDa |
| Null Reaction Comparator | 2.89 nm | 21 kDa |

Example 3. Synthesis of a Soluble High MW Chondroitin Sulfate Composition Modified With a Collagen-II Binding Peptide by Direct Reaction with DVS with Quenching Prior to Gel Formation A peptide-modified chondroitin sulfate can be prepared using methods described in the literature [Caravan, U.S. Pat. No. 9,386,938 B2] [Panitch, U.S. Pat. No. 9,200,039 B2]. The peptide-modified chondroitin sulfate (2.0 mmol equiv. hydroxyl groups) is dissolved in 2.25 mL DI water in an 8 mL reaction vessel to yield a clear colorless solution. DVS (0.067 g, 60 uL, 0.57 mmol) is added volumetrically with a microliter pipette and mixed gently to obtain a clear and colorless solution. Reaction is initiated by the addition of 0.25 mL of 1.0 N NaOH using a microliter pipette. The reaction is greater than 12 wt % in peptide-modified chondroitin sulfate and is 0.1 M in NaOH (pH 13). The reaction is gently mixed on a rotisserie. It becomes slightly more viscous over time but remains clear. At 20-40 minutes after the initiation of reaction, a rapid viscosity build may be observed and at that time, the reaction is quenched just prior to gelation by the addition of 0.25 mL of 1.0 N HCl. The pH after neutralization is approx. 5.0. The viscous reaction solution can be diluted with PBS to a total volume of 25 mL.

The diluted reaction solution can be analyzed using dynamic light scattering and compared to a control sample from a null reaction identical in all respects except for the omission of DVS. The product of Example 3 will have a significantly larger hydrodynamic radius and Mw relative to the null reaction comparator.

Example 4. Synthesis of a Soluble Chondroitin Sulfate/Carboxymethyl Cellulose Composition by Direct Reaction with DVS Carboxymethyl cellulose (0.050 g, 0.44 mmol equiv. hydroxyl groups) and chondroitin sulfate (0.600 g, 3.58 mmol equiv. hydroxyl groups) is dissolved in 4.5 mL DI water in an 8 mL reaction vessel. A clear colorless solution is obtained. DVS (0.100 g, 85 uL, 0.85 mmol) is added volumetrically with a microliter pipette. After gentle mixing, the solution is clear and colorless. Reaction is initiated by the addition of 0.5 mL of 1.0 N NaOH using a microliter pipette. With the addition of NaOH the solution immediately becomes pale yellow in color and remained clear. The reaction is 0.88 wt % in CMC, 10.62 wt % in chondroitin sulfate, and is 0.1 M in NaOH (approx. pH 13). The reaction is gently mixed on a rotisserie. It becomes more viscous over time and remains clear. Several minutes after the initiation of reaction, a rapid viscosity build is observed and the reaction is quenched by the addition of 0.25 mL of 1.0 N HCl. The pH after neutralization is found to be approx. 5.0. The viscous reaction solution is diluted with PBS to a total volume of 25 ml.

The diluted reaction solution is analyzed using dynamic light scattering and compared to a control sample from a null reaction identical in all respects except for the omission of DVS. The following hydrodynamic radii and Mw values are found (Table 3):

TABLE 3

| SAMPLE | Hydrodynamic Radius | Mw |
|---|---|---|
| Example 4 | Significantly larger radius than null | Significantly higher Mw than null |
| Null Reaction Comparator | 2.89 nm | 21 kDa |

Example 5. Synthesis of Soluble High MW Chondroitin Sulfate with a Bottlebrush-Like Architecture by the Staged Addition of Reactants in 1-Pot Sodium chondroitin sulfate (0.11 g, 0.66 mmol equiv. hydroxyl groups) was dissolved in 4.5 mL DI water in an 8 mL reaction vessel. A clear colorless solution was obtained. DVS (0.097 g, 82 uL, 0.82 mmol) was added volumetrically with a microliter pipette. After gentle mixing, the solution was clear and colorless. Reaction was initiated by the addition of 0.5 mL of 1.0 N NaOH using a microliter pipette. With the addition of NaOH the solution immediately became pale yellow in color and remained clear. The reaction is 2.15 wt % in chondroitin sulfate and is 0.1 M in NaOH (pH 13). The reaction was gently mixed on a rotisserie. After 30 minutes, additional sodium chondroitin sulfate was added (0.572 g, 3.41 mmol equiv. hydroxyl groups), and the reaction mixture was agitated on a rotisserie. The reaction solution became more viscous but remained clear. Five hours after the initiation, the reaction solution had not formed a gel. It remained a pale yellow clear and viscous solution and it was quenched by the addition of 0.5 mL of 1.0 N HCl. The pH after neutralization was found to be approx. 5.0.

A comparison reaction was performed (Table 4) in tandem in which all chondroitin sulfate (0.682 g, 4.1 mmol equiv. hydroxyl groups) was added in a single portion at the beginning of the reaction. This reaction mixture was also clear, pale yellow, and viscous. It built in viscosity and gelled after 52 minutes.

TABLE 4

| Reaction | Initial ChS wt % | Initial DVS/OH | Final ChS wt % | Final DVS/OH | Observations |
| --- | --- | --- | --- | --- | --- |
| Example 5 staged ChS addition | 2.15% | 1.24 | 12.0% | 0.20 | Viscous solution |
| Comparator | 12.0% | 0.20 | 12.0% | 0.20 | Stiff gel |

Example 6. Synthesis of Soluble High MW Proteoglycan Mimic Polymer with a Bottlebrush-Like Architecture by the Staged Addition of a CMC Followed by Chondroitin Sulfate in a 1-Pot Procedure Sodium carboxymethyl cellulose (250 kDa, 0.050 g, 0.44 mmol equiv. hydroxyl groups) is dissolved in 4.5 mL DI water in an 8 mL reaction vessel. A clear colorless solution is obtained. DVS (0.100 g, 85 uL, 0.85 mmol) is added volumetrically with a microliter pipette. After gentle mixing, the solution is clear and colorless. Reaction is initiated by the addition of 0.5 mL of 1.0 N NaOH using a microliter pipette. With the addition of NaOH the solution immediately becomes pale yellow in color and remained clear. The reaction is 0.88 wt % in CMC and is 0.1 M in NaOH (pH 13). The reaction is gently mixed on a rotisserie. After 30 minutes, sodium chondroitin sulfate is added (0.600 g, 3.58 mmol equiv. hydroxyl groups). The chondroitin sulfate dissolves entirely after approx. 5 minutes of agitation on a rotisserie. The reaction solution becomes more viscous but remains clear. 90 minutes after addition of the chondroitin sulfate, the clear viscous reaction solution is quenched by the addition of 0.5 mL of 1.0 N HCl. The pH after neutralization is found to be approx. 5.0.

The diluted reaction solution is analyzed using dynamic light scattering and compared to a control sample from a null reaction identical in all respects except for the omission of DVS. The product of Example 6 is found to have much larger hydrodynamic radius and Mw relative to the null reaction comparator.

Example 7. Synthesis of Soluble High MW Chondroitin Sulfate with a Bottlebrush-Like Architecture in a 2-Step Reaction Sequence 7A. Synthesis and Characterization of Vinylsulfone Modified Chondroitin Sulfate Sodium chondroitin sulfate (0.11 g, 0.66 mmol equiv. hydroxyl groups) was dissolved in 4.5 mL DI water in an 8 mL reaction vessel. A clear colorless solution was obtained. DVS (0.097 g, 82 uL, 0.82 mmol) was added volumetrically with a microliter pipette. After gentle mixing, the solution was clear and colorless. Reaction was initiated by the addition of 0.5 mL of 1.0 N NaOH using a microliter pipette. With the addition of NaOH the solution immediately became pale yellow in color and remained clear. The reaction was 2.15 wt % in chondroitin sulfate and was 0.1 M in NaOH (pH 13). The reaction was gently mixed on a rotisserie. After 30 minutes, the clear reaction solution was quenched by the addition of 0.5 mL of 1.0 N HCl. The reaction mixture was then added dropwise to a 50 ml conical centrifuge tube containing 25 ml of ethanol. A white solid was formed immediately. The solid was collected by centrifugation followed by removal of the supernatant. This solid was suspended in another 25 mL portion of ethanol in the same tube, shaken, and then centrifuged again. The solid was collected after removal of the supernatant and was placed under high vacuum to remove remaining ethanol and water.

The DVS-functionalized chondroitin sulfate can be characterized by H-NMR and the extent of DVS functionalization can be quantified by integration of the pendant vinyl groups.

7B. Formation of Soluble High MW Proteoglycan Mimic Polymer with a Bottlebrush-Like Architecture by the Reaction of Chondroitin Sulfate with Vinylsulfone Modified Chondroitin Sulfate The white solid formed in reaction 7A is dissolved in 4.5 mL DI water in an 8 mL reaction vessel. A clear colorless solution is obtained. Sodium chondroitin sulfate is added (0.572 g, 3.41 mmol equiv. hydroxyl groups), and the reaction mixture is agitated on a rotisserie for several minutes until all polymer dissolves. Reaction is initiated by the addition of 0.5 mL of 1.0 N NaOH using a microliter pipette. The reaction is gently mixed on a rotisserie. After 2-hours the reaction solution becomes more viscous but remains clear. The reaction is quenched by the addition of 0.5 mL of 1.0 N HCl. The pH after neutralization is found to be approx. 5.0. The viscous reaction solution is diluted with PBS to a total volume of 25 mL.

The diluted reaction solution can be analyzed using dynamic light scattering and compared to a control sample of the starting Chondroitin Sulfate material. The product of Example 7B will have much larger hydrodynamic radius and Mw relative to the starting material comparator.

Example 8. Synthesis of Soluble High MW CMC/Chondroitin Sulfate Composition with a Bottlebrush-Like Architecture in a 2-Step Reaction Sequence 8A. Synthesis and Characterization of Vinylsulfone Modified CMC Sodium carboxymethyl cellulose (250 kDa, 0.050 g, 0.44 mmol equiv. hydroxyl groups) was dissolved in 4.5 mL DI water in an 8 mL reaction vessel. A clear colorless solution was obtained. DVS (0.100 g, 85 uL, 0.85 mmol) was added volumetrically with a microliter pipette. After gentle mixing, the solution was clear and colorless. Reaction was initiated by the addition of 0.5 mL of 1.0 N NaOH using a microliter pipette. With the addition of NaOH the solution immediately become pale yellow in color and remained clear. The reaction was 0.88 wt % in CMC and was 0.1 M in NaOH (pH 13). The reaction was gently mixed on a rotisserie. After 30 minutes, the clear reaction solution was quenched by the addition of 0.5 mL of 1.0 N HCl. The reaction mixture was then added dropwise to a 50 mL conical centrifuge tube containing 25 mL of ethanol. A white solid was formed immediately. The solid was collected by centrifugation followed by removal of the supernatant. This solid was suspended in another 25 mL portion of ethanol in the same tube, shaken, and then centrifuged again. The solid was collected after removal of the supernatant and was placed under high vacuum to remove remaining ethanol and water.

The DVS-functionalized CMC can be characterized by H-NMR and the extent of DVS functionalization can be quantified by integration of the pendant vinyl groups.

8B. Formation of Soluble High MW Proteoglycan Mimic Polymer with a Bottlebrush-Like Architecture by the Reaction of Chondroitin Sulfate with Vinylsulfone Modified CMC The white solid formed in reaction 8A is dissolved in 4.5 mL DI water in an 8 mL reaction vessel. A clear colorless solution is obtained. Sodium chondroitin sulfate is added (0.572 g, 3.41 mmol equiv. hydroxyl groups), and the reaction mixture is agitated for several minutes until all polymer has dissolved. Reaction is initiated by the addition of 0.5 mL of 1.0 N NaOH using a microliter pipette. The reaction is gently mixed on a rotisserie. After 2-hours the reaction solution becomes more viscous but remains clear. The reaction is quenched by the addition of 0.5 mL of 1.0 N HCl. The pH after neutralization is found to be approx. 5.0. The viscous reaction solution is diluted with PBS to a total volume of 25 mL.

The diluted reaction solution can be analyzed using dynamic light scattering and compared to a control sample of the starting chondroitin sulfate material. It can also be compared to a solution of the CMC starting material. The product of Example 8B will have a significantly larger hydrodynamic radius and Mw relative to the two starting material comparators.

Example 9. Synthesis of Soluble High MW, Branched Chondroitin Sulfate Composition with a Bottlebrush-Like Architecture by the Staged Addition of Reactants in 1-Pot, with Purification of the Product Using Tangential Flow Filtration, and SEC Analysis of the Purified Isolated Product

9A. Reaction Via Staged Addition

Sodium chondroitin sulfate (0.153 g, 0.913 mmol equiv. hydroxyl groups) was dissolved in 4.865 g DI water in an 8 mL reaction vessel. A clear colorless solution was obtained. DVS (0.127 g, 108 uL, 1.07 mmol) was added volumetrically with a microliter pipette. After gentle mixing, the solution was clear and colorless. Reaction was initiated by the addition of 0.51 mL of 1.0 N NaOH using a microliter pipette. With the addition of NaOH, the solution immediately became pale yellow in color and remained clear. The reaction is 2.69 wt % in chondroitin sulfate and is 0.1 M in NaOH (pH 13). The reaction was gently mixed on a rotisserie. After 10 minutes, additional sodium chondroitin sulfate was added (0.454 g, 3.62 mmol equiv. hydroxyl groups), and the reaction mixture was agitated on a rotisserie. The reaction solution became more viscous but remained clear and fluid. Two hours after initiation by NaOH, the reaction was quenched by adding 0.51 mL of 1.0 N HCl using a microliter pipette. The clear fluid reaction mixture was added to a vial containing 30 g of PBS and the total weight was brought to 50 g with addition PBS.

9B. Purification Using Tangential Flow Filtration

A Spectrum Labs KR2i TFF system was used with a low volume feed reservoir (50 ml) and a 20-cm hollow fiber filter module containing modified polyethersulfone filter fibers (1 mm diameter, 100 kDa MWCO, 75 $cm^2$ total surface area, part #D02-E100-10-N). A sample of the diluted product of Example 9A (46 g) was loaded into the low volume feed reservoir. The tangential flow filtration was initiated at 100 ml/min flow rate, with flow rate increasing to 300 ml/min (50 ml/min increments) keeping the inlet pressure below 20 psig. TFF was run in dialysis mode in which the volume of solution lost to permeate was continuously made up with fresh deionized water. In this way, the volume of retentate solution remained constant during the filtration procedure as six volumes (270 ml) of permeate was generated. The deionized water replenishment was then suspended and the filtration was run in concentration mode to reduce the retentate volume down to approximately 30 mL. The TFF was then stopped and the system was flushed (10 ml DI water) to recover hold-up volume. The purified retentate (approx. 40 mL) was then dried by lyophilization for 72 hours, yielding purified product (0.251 g, 43% of starting chondroitin sulfate weight) as a white fluffy solid.

9C. Size Exclusion Chromatographic Analysis

SEC analysis was performed on an Agilent 1100 HPLC system equipped with an Agilent G1312 Binary Pump, G1322A Micro Degasser, G1367A Well-Plate Autosampler, G1316 Column Compartment, Wyatt Dawn EOS Multi-Angle Light Scattering Detector, and an OptiLab rEx Refractive Index Detector. A dn/dc value of 0.15 was used. The column chosen for separation was the TSK6000 plus guard column. Samples were diluted to a concentration of 5 mg/mL in PBS (pH=7.4), filtered through a 0.45 micron PVDF syringe filter and analyzed using the conditions in the Table 5 below.

TABLE 5

| Mobile Phase | PBS pH = 7.4 |
|---|---|
| Flow rate | 0.50 mL/min |
| Injection Volume | 10 μL |
| Column Temperature | 25° C. |

SEC analysis of the product was compared to that of the starting chondroitin sulfate material. The following results were obtained (Table 6):

TABLE 6

| | Chondroitin Sulfate (BioIberica EP Injectable Grade) | Example 9 (TFF Purified) |
|---|---|---|
| Mn (g/mol) | 13,490 | 91,110 |
| Mw (g/mol) | 14,270 | 250,000 |
| Mz (g/mol) | 15,310 | 704,000 |
| Rms radius Rn (nm) | 16.3 | 31.9 |
| Rms radius Rw (nm) | 17.0 | 35.4 |
| Rms radius Rz (nm) | 19.1 | 41.9 |
| Conformation Plot Slope* (nm mol/g) | 0.72 ± 0.12 | 0.53 ± 0.01 |

*Conformation plot slope is the slope of the linear log-log plot of rms radius (nm) vs. molar mass (g/mol). Rigid rod polymers can have a slope > 0.6 as seen for chondroitin sulfate. Branched or globular polymers have slopes < 0.6 with a theoretical lower limit of 0.33 for perfect spheres.

Example 9 demonstrates that the staged-addition reaction protocol produces a soluble polymer, filterable through a 0.45 um membrane, which can be purified by tangential flow filtration with a 100 kDa MWCO filter. The purified polymer was obtained in good yield, has a molecular weight significantly greater than the starting material, and has a branched conformation.

Example 10. Synthesis of Soluble High MW Chondroitin Sulfate Composition with a Bottlebrush-Like Architecture by the Staged Addition of Reactants in 1-Pot in the Presence of Sodium Chloride in Stage-2, and with Purification of the Product Using Tangential Flow Filtration, and SEC Analysis of the Purified Isolated Product 10A. Reaction Via Staged Addition with Salt in Stage-2

Sodium chondroitin sulfate (0.154 g, 0.920 mmol equiv. hydroxyl groups) was dissolved in 4.865 g DI water in an 8 mL reaction vessel. A clear colorless solution was obtained. DVS (0.127 g, 108 uL, 1.07 mmol) was added volumetrically with a microliter pipette. After gentle mixing, the solution was clear and colorless. Reaction was initiated by the addition of 0.51 mL of 1.0 N NaOH using a microliter pipette. With the addition of NaOH, the solution immediately became pale yellow in color and remained clear. The reaction is 3.07 wt % in chondroitin sulfate and is 0.1 M in NaOH (pH 13). The reaction was gently mixed on a rotisserie. After 20 minutes, additional sodium chondroitin sulfate was added (0.454 g, 3.63 mmol equiv. hydroxyl groups). Sodium chloride was also added (47.6 mg, 0.81 mmol) and the reaction mixture was agitated on a rotisserie. The reaction solution became more viscous but remained clear and fluid. Two hours after initiation by NaOH, the reaction was quenched by adding 0.51 mL of 1.0 N HCl using a microliter pipette. The clear fluid reaction mixture was added to a vial containing 30 g of PBS and the total weight was brought to 50 g with addition PBS. The diluted reaction mixture was easily filtered through a 0.45 um PVDF syringe filter.

10B. Purification Using Tangential Flow Filtration

A Spectrum Lab KR2i TFF system was used with a low volume feed reservoir (50 ml) and a 20-cm hollow fiber filter module containing modified polyethersulfone filter fibers (1 mm diameter, 100 kDa MWCO, 75 $cm^2$ total surface area, part #D02-E100-10-N). A sample of the diluted product of Example 10A was loaded into the low volume feed reservoir. The tangential flow filtration was initiated at 100 ml/min flow rate, with flow rate increasing to 300 ml/min (50 ml/min increments) keeping the inlet pressure below 25 psig. TFF was run in dialysis mode in which the volume of solution lost to permeate was continuously made up with fresh deionized water. In this way, the volume of retentate solution remained constant during the filtration procedure as greater than six volumes (>270 ml) of permeate was generated. The deionized water replenishment was then suspended and the filtration was run in concentration mode to reduce the retentate volume down to approximately 30 mL. The TFF was then stopped and the system was flushed (10 ml DI water) to recover hold-up volume. The purified retentate (approx. 40 mL) was then dried by lyophilization for 72 hours, yielding purified product as a white fluffy solid.

10C. Size Exclusion Chromatographic Analysis

SEC analysis was performed exactly as in example 9C. The following results were obtained (Table 7):

TABLE 7

|  | Chondroitin Sulfate (BioIberica EP Injectable Grade) | Example 10 (TFF Purified) |
| --- | --- | --- |
| Mn (g/mol) | 13,490 | 130,000 |
| Mw (g/mol) | 14,270 | 430,000 |
| Mz (g/mol) | 15,310 | 1,223,000 |
| Rms radius Rn (nm) | 16.3 | 36.6 |
| Rms radius Rw (nm) | 17.0 | 36.6 |
| Rms radius Rz (nm) | 19.1 | 46.5 |
| Branching Parameter* (nm mol/g) | 0.72 ± 0.12 | 0.48 ± 0.01 |

*Conformation plot slope is the slope of the linear log-log plot of rms radius (nm) vs. molar mass (g/mol). Rigid rod polymers can have a slope > 0.6 as seen for chondroitin sulfate. Branched or globular polymers have slopes < 0.6 with a theoretical lower limit of 0.33 for perfect spheres.

Example 10 demonstrates that the product of the staged-addition reaction protocol was a soluble polymer, filterable through a 0.45 um membrane, and purified by tangential flow filtration with a 100 kDa MWCO filter. The soluble polymer was obtained in good yield after TFF purification, has a molecular weight significantly greater than the starting material, and has a branched conformation. The addition of salt in stage-2 of the reaction resulted in a greater molecular weight relative to example 9.

Example 11. Synthesis of Soluble High MW Chondroitin Sulfate Composition with a Bottlebrush-Like Architecture by the Staged Addition of Reactants in 1-Pot in the Presence of Sodium Chloride (in Phase 1 and 2). Purification of the Product Using an Optimized Tangential Flow Filtration Protocol 11A. Reaction Via Staged Addition Sodium chondroitin sulfate (0.306 g, 1.823 mmol equiv. hydroxyl groups) and sodium chloride (85.2 mg, 1.46 mmol) were dissolved in 9.746 g DI water in a 20 mL reaction vessel. A clear colorless solution was obtained. DVS (0.254 g, 216 uL, 2.15 mmol) was added volumetrically with a microliter pipette. After gentle mixing, the solution was clear and colorless. Reaction was initiated by the addition of 1.03 mL of 1.0 N NaOH using a microliter pipette. With the addition of NaOH, the solution immediately became pale yellow in color and remained clear. The reaction is 3.04 wt % in chondroitin sulfate and is 0.1 M in NaOH (pH 13). The reaction was gently mixed on a rotisserie. After 15 minutes, additional sodium chondroitin sulfate was added (0.909 g, 7.25 mmol equiv. hydroxyl groups), and the reaction mixture was agitated on a rotisserie. The reaction solution became more viscous but remained clear and fluid. Two hours after initiation by NaOH, the reaction was quenched by adding 1.03 mL of 1.0 N HCl using a microliter pipette. The clear fluid reaction mixture was added to a vial containing 50 g of PBS and the total weight was brought to 80 g with addition PBS. The diluted reaction mixture was easily filtered through a 0.45 um PVDF syringe filter.

11B. Purification Using Tangential Flow Filtration

A Spectrum Lab KR2i TFF system was used with a 250 ml feed reservoir and a 20-cm hollow fiber filter module containing modified polyethersulfone filter fibers (1 mm diameter, 100 kDa MWCO, 75 cm² total surface area, part #D02-E100-10-N). The full 80 g portion of the diluted product of Example 11A was loaded into the feed reservoir. The tangential flow filtration was initiated at 200 ml/min flow rate, with flow rate increasing to 300 ml/min keeping the inlet pressure below 25 psig. TFF was run in dialysis mode in which the volume of solution lost to permeate was continuously made up with additional PBS. In this way, the volume of retentate solution remained constant during the filtration procedure as five volumes (400 ml) of permeate was generated. The TFF was then continued in desalting mode by replenishing the feed reservoir with DI water (instead of PBS) and continuing filtration until an additional five volumes of permeate (400 ml) was obtained. The DI water replenishment was then suspended and the filtration was run in concentration mode to reduce the retentate volume down to approximately 50 mL. The TFF was then stopped and the system was flushed (10 ml DI water) to recover hold-up volume. The purified retentate was then dried by lyophilization for 72 hours, yielding purified product (0.598 g, 45% yield relative to starting chondroitin sulfate weight) as a white fluffy solid.

Example 11 demonstrates that the staged-addition reaction protocol in the presence of 0.15M sodium chloride provides a soluble polymer, filterable through a 0.45 um membrane, and purified by tangential flow filtration with a 100 kDa MWCO filter. The soluble polymer was obtained in good yield after TFF purification. It is expected to have a molecular weight significantly greater than the starting material, and a branched conformation. Furthermore, the addition of salt is expected to result in a greater molecular weight relative to examples 9 and 10.

Example 12. Synthesis of Soluble High MW Chondroitin Sulfate Composition with a Bottlebrush-Like Architecture Containing a Galactosyl Epitope

12A. Reaction Via Staged Addition

Sodium chondroitin sulfate (0.306 g, 1.823 mmol equiv. hydroxyl groups) and sodium chloride (85.2 mg, 1.46 mmol) are dissolved in 9.746 g DI water in a 20 mL reaction vessel. A clear colorless solution is obtained. DVS (0.254 g, 216 uL, 2.15 mmol) is added volumetrically with a microliter pipette. After gentle mixing, the solution is clear and colorless. Reaction is initiated by the addition of 1.03 mL of 1.0 N NaOH using a microliter pipette. With the addition of NaOH, the solution immediately becomes pale yellow in color but remains clear. The reaction is 3.04 wt % in chondroitin sulfate and is 0.1 M in NaOH (pH 13). The reaction is gently mixed on a rotisserie. After 15 minutes, additional sodium chondroitin sulfate (0.909 g, 7.25 mmol equiv. hydroxyl groups), and lactosylamine (36.5 mg, 0.107 mmol) are added. The reaction mixture is agitated on a rotisserie. The reaction solution becomes slightly more viscous but remains clear and fluid. Two hours after initiation by NaOH, the reaction is quenched by adding 1.03 mL of 1.0 N HCl using a microliter pipette. The clear fluid reaction mixture is added to a vial containing 50 g of PBS and the total weight is brought to 80 g with addition PBS. The diluted reaction mixture is easily filtered through a 0.45 um PVDF syringe filter.

12B. Purification Using Tangential Flow Filtration

A Spectrum Lab KR2i TFF system is used with a 250 ml feed reservoir and a 20-cm hollow fiber filter module containing modified polyethersulfone filter fibers (1 mm diameter, 100 kDa MWCO, 75 cm² total surface area, part #D02-E100-10-N). The full 80 g portion of the diluted product of Example 12A is loaded into the feed reservoir. Tangential flow filtration is initiated at 200 ml/min flow rate, with flow rate increasing to 300 ml/min keeping the inlet pressure below 25 psig. TFF is run in dialysis mode in which the volume of solution lost to permeate is continuously made up with additional PBS. In this way, the volume of retentate solution remains constant during the filtration procedure as five volumes (400 ml) of permeate is generated. The TFF is then continued in desalting mode by replenishing the feed reservoir with DI water and continuing filtration until an additional five volumes of permeate (400 ml) is obtained. The deionized water replenishment is then suspended and the filtration is run in concentration mode to reduce the retentate volume down to approximately 50 mL. The TFF 15 then stopped and the system is flushed (10 ml DI water) to recover hold-up volume. The purified retentate is then dried by lyophilization for 72 hours, yielding purified product in good yield as a white fluffy solid.

12C. Analysis of the High Molecular Weight Chondroitin Sulfate Lactosylamine Conjugate The purified product of Example 12 can be analyzed by SEC-MALLS as described for examples 9, and 10. The level of lactosylamine incorporation in the purified product can be determined by exhaustive hydrolysis followed by analysis of the resulting mixture of monosaccharides by high-performance anion-exchange chromatography using a pulse amperometric detection. For example, the samples can be hydrolyzed in 2 M trifluoroacetic acid at 100° C. for 8 hours and the hydrolysates dried in a speed-vac. The resulting residue can be dissolved in water and analyzed on a Carbo Pac PA-1 column with 16 mM sodium hydroxide eluent (isocratic).

Example 12 illustrates how a high molecular weight chondroitin sulfate composition bearing galactose epitopes can be prepared, purified by TFF, and characterized. As exemplified here, the inventive chemical process for producing high molecular weight branched sulfated GAGs can be carried out in the presence of other biological epitopes in the second stage that are capable of reacting with the DVS-modified intermediate prepared in the first stage.

Example 13. Synthesis of Soluble High MW Chondroitin Sulfate Composition Modified with a Collagen-II Binding Peptide

13A. Reaction Via Staged Addition

Sodium chondroitin sulfate (0.306 g, 1.823 mmol equiv. hydroxyl groups) and sodium chloride (85.2 mg, 1.46 mmol) are dissolved in 9.746 g DI water in a 20 mL reaction vessel. A clear colorless solution is obtained. DVS (0.254 g, 216 uL, 2.15 mmol) is added volumetrically with a microliter pipette. After gentle mixing, the solution is clear and colorless. Reaction is initiated by the addition of 1.03 mL of 1.0 N NaOH using a microliter pipette. With the addition of NaOH, the solution immediately becomes pale yellow in color but remains clear. The reaction is 3.04 wt % in chondroitin sulfate and is 0.1 M in NaOH (pH 13). The reaction is gently mixed on a rotisserie. After 15 minutes, a peptide modified chondroitin sulfate (7.25 mmol equiv. hydroxyl groups) are added. The reaction mixture is agitated on a rotisserie. The reaction solution becomes slightly more viscous but remains clear and fluid. Two hours after initiation by NaOH, the reaction is quenched by adding 1.03 mL of 1.0 N HCl using a microliter pipette. The clear fluid reaction mixture is added to a vial containing 50 g of PBS and the total weight is brought to 80 g with addition PBS. The diluted reaction mixture is easily filtered through a 0.45 um PVDF syringe filter.

13B. Purification Using Tangential Flow Filtration

A Spectrum Lab KR2i TFF system is used with a 250 ml feed reservoir and a 20-cm hollow fiber filter module containing modified polyethersulfone filter fibers (1 mm diameter, 100 kDa MWCO, 75 cm² total surface area, part #D02-E100-10-N). The full 80 g portion of the diluted product of Example 12A is loaded into the feed reservoir. Tangential flow filtration is initiated at 200 ml/min flow rate, with flow rate increasing to 300 ml/min keeping the inlet pressure below 25 psig. TFF is run in dialysis mode in which the volume of solution lost to permeate is continuously made up with additional PBS. In this way, the volume of retentate solution remains constant during the filtration procedure as five volumes (400 ml) of permeate is generated. The TFF is then continued in desalting mode by replenishing the feed reservoir with DI water and continuing filtration until an additional five volumes of permeate (400 ml) is obtained. The deionized water replenishment is then suspended and the filtration is run in concentration mode to reduce the retentate volume down to approximately 50 mL. The TFF 15 then stopped and the system is flushed (10 ml DI water) to recover hold-up volume. The purified retentate is then dried by lyophilization for 72 hours, yielding purified product in good yield as a white fluffy solid.

Example 13 illustrates how a high molecular weight chondroitin sulfate composition bearing a collagen-II binding peptide epitope can be prepared, and purified by TFF. Various peptide-modified chondroitin sulfate materials can be prepared using methods described in the literature [Caravan, U.S. Pat. No. 9,386,938 B2] [Panitch, U.S. Pat. No. 9,200,039 B2]. As exemplified here, the inventive chemical process for producing high molecular weight branched sulfated GAGs can be carried out with chemically modified GAGs bearing various peptide moieties or other biological epitopes.

Example 14. Evaluation of High MW Chondroitin Sulfate Compositions with Bottlebrush-Like Architectures in a Rat Model of Interstitial Cystitis A rat model is used to replicate the leaky bladder pathology that is understood to be a major contributor in the development of interstitial cystitis (IC). Female ovariectomized (OVX) Sprague-Dawley rats (250-300 g) are purchased from Charles River Laboratories. Rats are housed two per cage under controlled temperature and humidity. OVX rats are used to avoid any effects of hormonal cycling, and because male rats cannot be catheterized through the urethra. All animals have free access to food and water and are acclimated to the facility housing for a minimum of 1 week before experimentation. The experimental protocol is approved by the relevant Institutional Animal Care and Use Committee.

Transurethral Protamine Sulfate (PS) Treatment

OVX female SAS Sprague Dawley® rats at age 7-weeks weighing 250 to 300 grams are treated with protamine sulfate (PS) to induce leaky bladder as described in the literature [Towner, et. al., Journal of Urology 2015, vol 193, pp 1394-1400]. Rats are anesthetized with isoflurane (3%) with a steady supply of oxygen for a period of approximately 10 min, and the bladder is emptied following catheterization using a lubricated 18-gauge intravenous catheter (Surflo, Terumo, Elkton, MD) and a custom-made guide wire. Care is taken not to traumatize the bladder by stopping the catheter just after it passes by the pubic bones and not allowing it to "bottom out." Animals are monitored for hematuria as an indicator of bladder trauma, and any animals with blood in the urine or solutions are not used. PS (1 mg/ml in 400 µl saline) is slowly instilled into the bladder through the catheter. After 15 min, the bladder is emptied by applying lower abdominal pressure. The bladders are then rinsed with saline (400 µl×3), after which the transurethral catheter is removed and animals are returned to their home cages.

MRI Imaging of Bladder and Colon

Bladder permeability is assessed by Magnetic Resonance Imaging (MRI). Rats are anesthetized with isoflurane (1.5% to 3.0%) with 800 to 1,000 ml O2 for MRI experiments. MM is performed on a 7-Tesla 30 cm bore BioSpec® MRI system. For bladder images, in vivo diagnostic CE-MM specifically uses Gd-DTPA (0.2 mmol Gd/kg diluted to 800 ml in saline) administered via an intravesical catheter to visualize bladder urothelium loss of permeability on bladder contrast images. Bladder contrast images are obtained every 3 minutes 43 seconds for a total of 20 minutes. For colon contrast images, Gd-DTPA (0.2 mmol Gd/kg diluted to 200 ml in saline) is administered intravenously via a 24 gauge 0.75-inch BD Insyte™ Autoguard™ shielded intravenous tail vein catheter. Images are obtained for 30 minutes. All MM images are acquired using a T1-weighted RARE (rapid acquisition with relaxation enhancement) MRI pulse sequence with certain parameters, including repetition time 1,200 milliseconds, echo time 9 milliseconds, a RARE factor of 4, 4 averages, 1 mm image slice thickness, 256× 256 matrix and 6.5×6.5 cm2 field of view with motion and fat suppression.

Biopolymer Treatment

Chondroitin sulfate based biopolymers are instilled into the leaky bladder 24 hours after PS treatment. There are 3 treatment groups with 10-rats per group (n=10): Group-A, a high molecular weight chondroitin sulfate with bottlebrush architecture from Example 11; Group-B, high molecular weight chondroitin sulfate with bottlebrush architecture bearing a galactosyl epitope from Example 12; Group-C, a saline treated control. The biopolymers are administered via transurethral catheterization 24 hrs. after PS exposure. The biopolymers are dissolved in saline (20 mg/ml) and sterile filtered (0.2 µm PVDF syringe filter) prior to administration. Biopolymer administration is performed under the anesthesia protocol described for the MRI imaging.

MRI is performed 24 hours after PS exposure, immediately after polymer treatment. MRI is performed again 5-days following PS exposure, 4-days after biopolymer treatment.

Data Analysis and Statistics

MRI signal intensity was measured from regions of interest (ROIs) in images. Four or 5 ROIs are used in high intensity regions in the bladder periphery, colon mucosa, adipose body surrounding the bladder, surrounding colon tissues and medial thigh muscle along with corresponding regions in control data sets. These data are displayed using ParaVision™, version 5.0. Statistical analysis is done using ANOVA with the post Tukey multiple comparison test to evaluate differences in treatment groups using InStat (GRAPH-PAD®). Signal intensity differences between groups with p<0.05, <0.01 or <0.001 is considered statistically significant.

Example 14 demonstrates how the inventive high molecular weight chondroitin sulfate compositions with bottlebrush architecture with and without galactose epitopes restore impermeability to leaky bladder in the rat protamine sulfate model. Animals treated with the inventive materials prepared in examples 11 and 12 will show significantly greater bladder impermeability (less leak) relative to animals treated with saline.

Example 15 Variation of Chondroitin Sulfate/DVS Molar Ratio: An Observational Study A set of reaction vials were each filled with various amounts of sodium chondroitin sulfate and DI water to provide solutions at 4, 6, 8, and 10 wt % chondroitin sulfate. The vials were gently agitated on a rotisserie mixer resulting in a set of clear colorless solutions. Various amounts of DVS were then added volumetrically to each vial with a microliter pipette such that for each concentration of chondroitin sulfate, the molar ratios of DVS to available chondroitin sulfate hydroxyl groups were: 0.98, 0.65 and 0.32. After gentle mixing, all solutions were clear and colorless. Reaction was initiated by the addition of 1.0 N NaOH using a microliter pipette. With the addition of NaOH the solution immediately became pale yellow in color and remained clear. Each reaction was 0.1M in NaOH (approx. pH 13). The set of 12 reactions were gently mixed on a rotisserie and observed over time for gelation and for loss of clarity. Loss of clarity was judged by a visual determination of the development of haziness or opacity. Gelation was judged by visual determination of loss of flow. When a reaction formed a non flowable gel, the gel time was noted. FIG. 5 illustrates the compositions of these 12 reactions and the observations made on homogeneity and flowability for each.

Example 16 Variation of Carboxymethylcellulose/DVS Molar Ratio: An Observational Study A set of reaction vials were each filled with various amounts of CMC and DI water to provide solutions at 1, 2, 3, 4, 5, and 6 wt % CMC. The vials were gently agitated on a rotisserie mixer resulting in a set of clear colorless solutions. Various amounts of DVS were then added volumetrically to each vial with a microliter pipette such that for each concentration of CMC, the molar ratios of DVS to available CMC hydroxyl groups were: 1.2, 0.6 and 0.3. After gentle mixing, all solutions were clear and colorless. Reaction was initiated by the addition of 1.0 N NaOH using a microliter pipette. With the addition of NaOH the solution immediately became pale yellow in color and remained clear. Each reaction was 0.1M in NaOH (approx. pH 13). The set of 18 reactions were gently mixed on a rotisserie and observed over time for gelation and for loss of clarity. Loss of clarity was judged by a visual determination of the development of haziness or opacity. Gelation was judged by visual determination of loss of flow. When a reaction formed a non flowable gel, the gel time was noted. FIG. 6 illustrates the compositions of these 18 reactions and the observations made on homogeneity and flowability for each.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

---

What is claimed is:

1. A water-soluble branched polymer conjugate comprising a plurality of sulfated glycosaminoglycan (GAG) polymer chains, wherein each sulfated GAG polymer chain is linked to one or more sulfated GAG polymer chains via a linker derived from divinylsulfone, and wherein the polymer conjugate is soluble in aqueous solution and has a molecular weight that is 3× to 100× that of an individual, nonlinked sulfated GAG.

2. The polymer conjugate of claim 1, wherein the sulfated GAG is selected from the group consisting of chondroitin sulfate, heparan sulfate, dermatan sulfate, keratan sulfate, and combinations thereof.

3. The polymer conjugate of claim 1, wherein the linker is randomly linked along a GAG polymer chain.

4. A method of preparing the conjugate of claim 1, via sequential introduction of the sulfated GAG in a single reaction, comprising the steps of:
  i) providing an aqueous sulfated GAG solution; and
  ii) reacting the aqueous sulfated GAG solution with divinylsulfone under conditions where a small portion of the sulfated GAG is reacted with the full portion of divinylsulfone; and
  iii) adding the remaining portion of sulfated GAG to form a conjugate with a branched conformation.

5. The conjugate of claim 1, wherein at least one GAG polymer chain comprises at least one modifier selected from a binding modifier and a therapeutic modifier.

6. The conjugate of claim 5, wherein the binding modifier is a collagen-binding modifier, a glycan ligand for galectins binding modifier, or a glycan ligand for galectins comprising β-galactoside.

7. The conjugate of claim 5, wherein the therapeutic modifier is an anti-oxidant modifier.

8. A method of treating a disease, disorder, or condition associated with a soft tissue in a subject comprising administering to a subject a conjugate of claim 1.

9. A method of treating Interstitial Cystitis (IC) in a patient comprising the step of administering to the patient, a conjugate of claim 1.

10. The method of claim 9, wherein administration is intravesical instillation.

11. A method of claim 4, wherein the product of step (ii) is isolated.

12. A method of claim 4, wherein the soluble branched polymer has a molecular weight of 15,000 Da to 1,000,000 Da.

13. A method of claim 4, wherein the molar ratio of divinylsulfone to GAG hydroxyl groups is 0.01 to 0.6.

* * * * *